(12) United States Patent
Filev et al.

(10) Patent No.: US 9,811,935 B2
(45) Date of Patent: Nov. 7, 2017

(54) EMOTIVE ADVISORY SYSTEM AND METHOD

(75) Inventors: Dimitar Petrov Filev, Novi, MI (US); Oleg Yurievitch Gusikhin, West Bloomfield, MI (US); Erica Klampfl, Canton, MI (US); Yifan Chon, Ann Arbor, MI (US); Fazal Urrahman Syed, Canton, MI (US); Perry Macneille, Lathrup Village, MI (US); Mark Schunder, Dearborn, MI (US); Thomas Giuli, Ann Arbor, MI (US); Basavaraj Tonshal, Livonia, MI (US)

(73) Assignee: Ford Global Technologies, LLC, Dearborn, MI (US)

( * ) Notice: Subject to any disclaimer, the term of this patent is extended or adjusted under 35 U.S.C. 154(b) by 3054 days.

(21) Appl. No.: 12/110,712

(22) Filed: Apr. 28, 2008

(65) Prior Publication Data

US 2008/0269958 A1    Oct. 30, 2008

Related U.S. Application Data

(60) Provisional application No. 60/914,152, filed on Apr. 26, 2007.

(51) Int. Cl.
*G05D 1/00* (2006.01)
*G05D 3/00* (2006.01)
(Continued)

(52) U.S. Cl.
CPC .............. *G06T 13/40* (2013.01); *A61B 5/165* (2013.01); *A61B 5/18* (2013.01); *A61B 5/4803* (2013.01);
(Continued)

(58) Field of Classification Search
USPC .............................................................. 701/1
See application file for complete search history.

(56) References Cited

U.S. PATENT DOCUMENTS

| 5,495,720 A | 3/1996 | Buck |
|---|---|---|
| 6,079,220 A | 6/2000 | Buck |
| (Continued) | | |

FOREIGN PATENT DOCUMENTS

| EP | 0893308 A2 | 1/1999 |
|---|---|---|
| EP | 1123843 A2 | 8/2001 |
| (Continued) | | |

OTHER PUBLICATIONS

Dimitar Filev, et al., Context Dependent Information Aggreagation, the IEEE International Conference on Fuzzy Systems, 2003, pp. 672-677.

(Continued)

*Primary Examiner* — Imran Mustafa
(74) *Attorney, Agent, or Firm* — Jennifer Stec; Brooks Kushman P.C.

(57) ABSTRACT

Information about a device may be emotively conveyed to a user of the device. Input indicative of an operating state of the device may be received. The input may be transformed into data representing a simulated emotional state. Data representing an avatar that expresses the simulated emotional state may be generated and displayed. A query from the user regarding the simulated emotional state expressed by the avatar may be received. The query may be responded to.

12 Claims, 13 Drawing Sheets

(51) Int. Cl.

| | | |
|---|---|---|
| *G06F 7/00* | (2006.01) | |
| *G06F 17/00* | (2006.01) | |
| *G06T 13/40* | (2011.01) | |
| *B60W 50/10* | (2012.01) | |
| *G01C 21/36* | (2006.01) | |
| *G06F 3/01* | (2006.01) | |
| *G06N 3/00* | (2006.01) | |
| *G10L 17/26* | (2013.01) | |
| *G06T 13/20* | (2011.01) | |
| *A61B 5/16* | (2006.01) | |
| *A61B 5/18* | (2006.01) | |
| *B60W 40/08* | (2012.01) | |
| *A61B 5/00* | (2006.01) | |

(52) U.S. Cl.
CPC ............. *A61B 5/744* (2013.01); *B60W 50/10* (2013.01); *G01C 21/3608* (2013.01); *G06F 3/011* (2013.01); *G06N 3/006* (2013.01); *G06T 13/205* (2013.01); *G10L 17/26* (2013.01); *A61B 5/7264* (2013.01); *B60W 2040/089* (2013.01); *G06F 2203/011* (2013.01)

(56) References Cited

U.S. PATENT DOCUMENTS

| | | | |
|---|---|---|---|
| 6,249,720 B1 * | 6/2001 | Kubota | ............... B60R 16/0232 340/990 |
| 6,351,698 B1 | 2/2002 | Kubota et al. | |
| 6,757,593 B2 | 6/2004 | Mori et al. | |
| 6,817,979 B2 | 11/2004 | Nihtila | |
| 7,020,544 B2 | 3/2006 | Shinada | |
| 2002/0002464 A1 | 1/2002 | Petrushin | |
| 2002/0138181 A1 | 9/2002 | Mori | |
| 2003/0046689 A1 | 3/2003 | Gaos | |
| 2004/0002634 A1 | 1/2004 | Nihtila | |
| 2004/0250210 A1 | 12/2004 | Huang | |
| 2005/0060158 A1 | 3/2005 | Endo et al. | |
| 2005/0101845 A1 | 5/2005 | Nihtila | |
| 2005/0143915 A1 | 6/2005 | Odagawa et al. | |
| 2005/0197765 A1 | 9/2005 | Kido et al. | |
| 2005/0216529 A1 | 9/2005 | Ashtekar | |
| 2005/0223328 A1 | 10/2005 | Ashtekar | |
| 2005/0248574 A1 | 11/2005 | Ashtekar | |
| 2006/0122834 A1 * | 6/2006 | Bennett | ............... G10L 15/1822 704/256 |
| 2006/0155665 A1 | 7/2006 | Sekiyama | |
| 2007/0074114 A1 | 3/2007 | Adjali | |

FOREIGN PATENT DOCUMENTS

| | | |
|---|---|---|
| EP | 1431127 A1 | 6/2004 |
| GB | 2379787 A | 3/2003 |
| JP | 11037766 A | 2/1999 |
| JP | 11250395 A | 9/1999 |
| JP | 11259271 A | 9/1999 |
| JP | 11259446 A | 9/1999 |
| JP | 11272639 A | 10/1999 |
| JP | 11272640 A | 10/1999 |
| WO | 2005027091 A1 | 3/2005 |
| WO | 2006108617 A2 | 10/2006 |
| WO | 2006136897 A1 | 12/2006 |
| WO | 2007054284 A1 | 5/2007 |
| WO | 2007090593 A1 | 8/2007 |

OTHER PUBLICATIONS

Guido Hartmann, The virtual Carla points the Way, News wams_print-World Online, Dec. 2, 2007.

Joseph Ogando, These Best Faces, Design News, Feb. 26, 2007, pp. 54-56, 58.

Written Opinion of the International Searching Authority, dated Aug. 8, 2008, in International Application No. PCT/US2008/061759.

Affective Media, http://web.archive.org/web/20070403090630/http://www.affectivemedia.com/technology.htm, Apr. 3, 2007.

Luc Steels, Frederic Kaplan, "AIBO's first words. The social learning of language and meaning", pp. 1-35, printed Oct. 16, 2005.

Frederic Kaplan, "Free creatures: The role of uselessness in the design of artificial pets", pp. 1-3, Sep. 2000.

Ing-Marie Jonsson, Clifford Nass, Jack Endo, Ben Reaves, Helen Harris, Janice Le Ta, Nicholas Chan, Sean Knapp, "Don't Blame me I am Only the Driver: Impact of Blame Attribution on Attitudes and Attention to Driving Task", CHI 2004—Late Breaking Results Paper, Apr. 24-29, Vienna, Austria, pp. 1219-1222.

Terrence Fong, Illah Nourbakhsh, Kerstin Dautenhahn, "A survey of socially interactive robots", Elsevier 2003 Science B.V., Robotics and Autonomous Systems 42 (2003) 143-166.

Clifford Nass, Ing-Marie Jonsson, Helen Harris, Ben Reaves, Jack Endo, Scott Brave, Leila Takayama, "Improving Automotive Safety by Pairing Driver Emotion and Car Voice Emotion", CHI 2005, Late Breaking Results: Short Papers, Apr. 2-7, Portland, Oregon, pp. 1973-1976.

Frederic Kaplan, "Talking AIBO: First Experimentation of Verbal Interactions with an Autonomous Four-Legged Robot", pp. 1-7, Oct. 2000.

Ing-Marie Jonsson, Mary Zajicek, Helen Harris, Clifford Nass, "Thank You, I did not see that: In-car Speech Based Information Systems for Older Adults", CHI 2005, Apr. 2-7, 2004, Portland, Oregon, pp. 1-4.

Masahiro Fujita, "On Activating Human Communications with Pet-Type Robot AIBO", Proceedings of the IEEE, vol. 92, No. 11, Nov. 2004, pp. 1804-1813.

Masahiro Fujita, Hiroaki Kitano, "Development of an Autonomous Quadruped Robot for Robot Entertainment", Autonomous Robots, 5, 7-18 (1998), 1998 Kluwer Academic Publishers, Boston, Manufactured in the Netherlands.

* cited by examiner

EMOTIVE ADVISORY SYSTEM AND METHOD

CROSS-REFERENCE TO RELATED APPLICATION

This application claims the benefit of U.S. Provisional Application No. 60/914,152 filed Apr. 26, 2007.

BACKGROUND

U.S. Pub. No. 2007/0074114 to Adjali et al. discloses a human-computer interface for automatic persuasive dialog between the interface and a user and a method of operating such an interface. The method includes presenting a user with an avatar or animated image for conveying information to the user and receiving real time data relating to a personal attribute of the user, so as to modify the visual appearance and/or audio output of the avatar or animated image as a function of the received data relating to a personal attribute of the user.

SUMMARY

A method for emotively conveying information to a user of a device may include receiving input indicative of an operating state of the device, transforming the input into data representing a simulated emotional state and generating data representing an avatar that expresses the simulated emotional state. The method may also include displaying the avatar, receiving a query from the user regarding the simulated emotional state expressed by the avatar and responding to the query.

DETAILED DESCRIPTION

Figure 1:
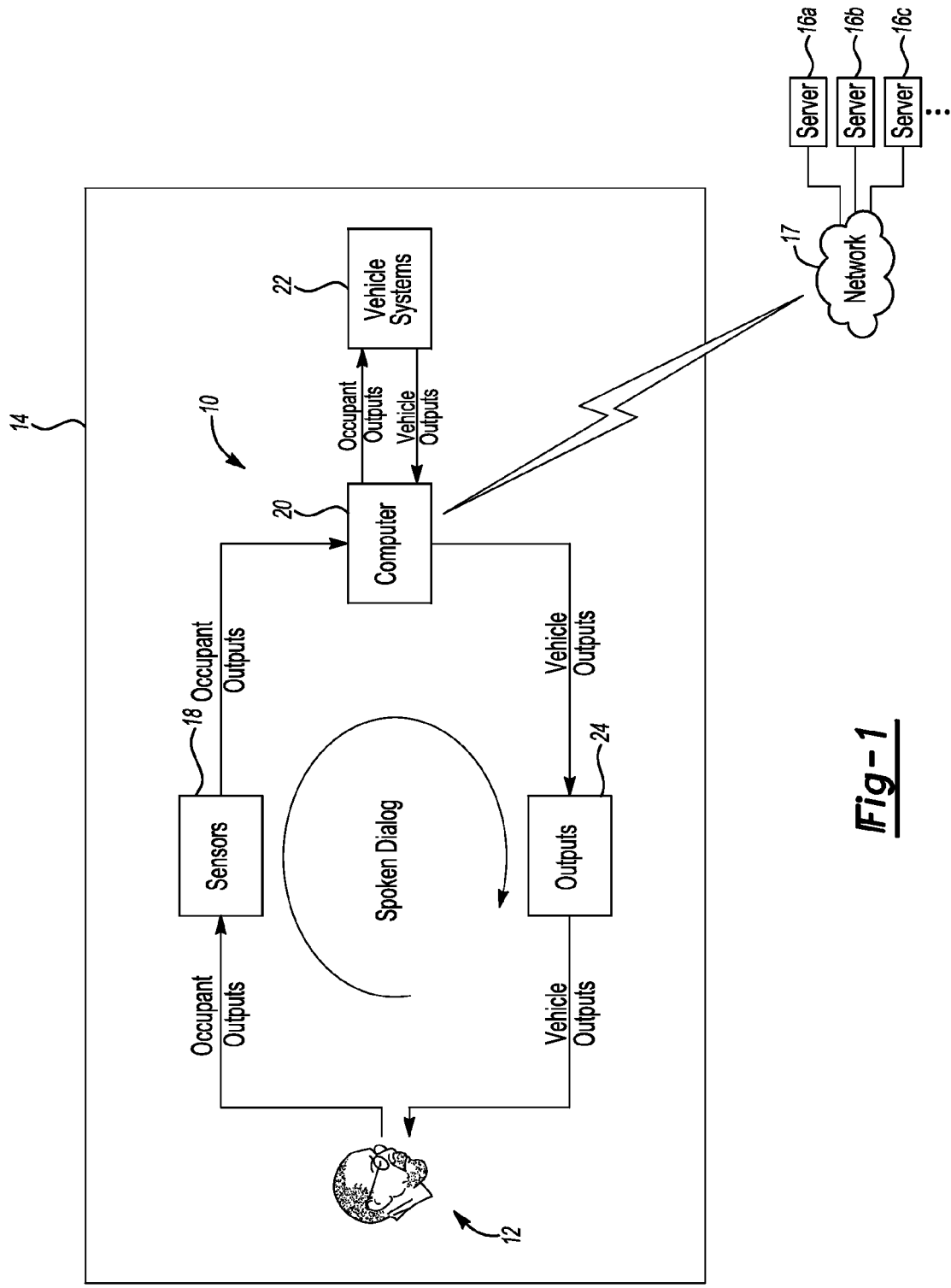
FIG. 1 is a block diagram of an embodiment of an emotive advisory system for an automotive vehicle.

Referring now to FIG. 1, an embodiment of an emotive advisory system (EAS) 10, inter alia, assists an occupant/user 12 of a vehicle 14 in operating the vehicle 14 and in accessing information sources 16n, e.g., web servers, etc., remote from the vehicle 14 via a network 17. Of course, other embodiments of the EAS 10 may be implemented within the context of any type of device and/or machine. For example, the EAS 10 may accompany a household appliance, hand held computing device, etc. Certain embodiments of the EAS 10 may be implemented as an integrated module that may be docked with another device and/or machine. A user may thus carry their EAS 10 with them and use it to interface with devices and/or machines they wish to interact with. Other configurations and arrangements are also possible.

In the embodiment of FIG. 1, sensors 18 detect inputs generated by the occupant 12 and convert them into digital information for a computer 20. The computer 20 receives these inputs as well as inputs from the information sources 16n and vehicle systems 22. The computer 20 processes these inputs and generates outputs for at least one of the occupant 12, information sources 16n and vehicle systems 22. Actuators/outputs, etc. 24 convert the outputs for the occupant 12 from a digital format into a format that may be perceived by the occupant 12, whether visual, audible, tactile, haptic, etc.

The occupant 12 may, in some embodiments, communicate with the EAS 10 through spoken dialog that follows rules of discourse. For example, the occupant 12 may ask "Are there any good restaurants in the area?" In response, the EAS 10 may query appropriate information sources 16n and, together with geographic location information from the vehicle systems 22, determine a list of highly rated restaurants near the current location of the vehicle 14. The EAS 10 may answer with the simulated dialog: "There are a few. Would you like to hear the list?" An affirmative response from the occupant 12 may cause the EAS 10 to read the list.

The occupant 14 may also command the EAS 10 to alter certain parameters associated with the vehicle systems 22. For example, the occupant 14 may state "I feel like driving fast today." In response, the EAS 10 may ask "Would you like the drivetrain optimized for performance driving?" An affirmative response from the occupant 12 may cause the EAS 10 to alter engine tuning parameters for enhanced performance.

In some embodiments, the spoken dialog with the EAS 10 may be initiated without pressing any buttons or otherwise physically providing input to the EAS 10. This open microphone functionality allows the occupant 12 to initiate a conversation with the EAS 10 in the same way the occupant 12 would initiate a conversation with another occupant of the vehicle 14.

The occupant 12 may also "barge in" on the EAS 10 while it is speaking. For example, while the EAS 10 is reading the list of restaurants mentioned above, the occupant 12 may interject "Tell me more about restaurant X." In response, the EAS 10 may cease reading the list and query appropriate information sources 16*n* to gather additional information regarding restaurant X. The EAS 10 may then read the additional information to the occupant 12.

In some embodiments, the actuators/outputs 24 include a screen that selectively displays an avatar. The avatar may be a graphical representation of human, animal, machine, plant, vehicle, etc. and may include features, e.g., a face, etc., that are capable of visually conveying emotion. The avatar may be hidden from view if, for example, a speed of the vehicle 14 is greater than a threshold which may be manufacturer or user defined. The avatar's voice, however, may continue to be heard. Of course, any suitable type of display technology, such as a holographic or head-up display, may be used.

The avatar's simulated human emotional state may depend on a variety of different criteria including an estimated emotional state of the occupant 12, a condition of the vehicle 14 and/or a quality with which the EAS 10 is performing a task, etc. For example, the sensors 18 may detect head movements, speech prosody, biometric information, etc. of the occupant 12 that, when processed by the computer 20, indicate that the occupant 12 is angry. In one example response, the EAS 10 may limit or discontinue dialog that it initiates with the occupant 12 while the occupant 12 is angry. In another example response, the avatar may be rendered in blue color tones with a concerned facial expression and ask in a calm voice "Is something bothering you?" If the occupant 12 responds by saying "Because of this traffic, I think I'm going to be late for work," the avatar may ask "Would you like me to find a faster route?" or "Is there someone you would like me to call?" If the occupant 12 responds by saying "No. This is the only way . . . ," the avatar may ask "Would you like to hear some classical music?" The occupant 12 may answer "No. But could you tell me about the upcoming elections?" In response, the EAS 10 may query the appropriate information sources 16*n* to gather the current news regarding the elections. During the query, if the communication link with the information sources 16*n* is strong, the avatar may appear happy. If, however, the communication link with the information sources 16*n* is weak, the avatar may appear sad, prompting the occupant to ask "Are you having difficulty getting news on the elections?" The avatar may answer "Yes, I'm having trouble establishing a remote communication link."

During the above exchange, the avatar may appear to become frustrated if, for example, the vehicle 14 experiences frequent acceleration and deceleration or otherwise harsh handling. This change in simulated emotion may prompt the occupant 14 to ask "What's wrong?" The avatar may answer "Your driving is hurting my fuel efficiency. You might want to cut down on the frequent acceleration and deceleration." The avatar may also appear to become confused if, for example, the avatar does not understand a command or query from the occupant 14. This type of dialog may continue with the avatar dynamically altering its simulated emotional state via its appearance, expression, tone of voice, word choice, etc. to convey information to the occupant 12.

The EAS 10 may also learn to anticipate requests, commands and/or preferences of the occupant 12 based on a history of interaction between the occupant 12 and the EAS 10. For example, the EAS 10 may learn that the occupant 12 prefers a cabin temperature of 72° Fahrenheit when ambient temperatures exceed 80° Fahrenheit and a cabin temperature of 78° Fahrenheit when ambient temperatures are less than 40° Fahrenheit and it is a cloudy day. A record of such climate control settings and ambient temperatures may inform the EAS 10 as to this apparent preference of the occupant 12. Similarly, the EAS 10 may learn that the occupant 12 prefers to listen to local traffic reports upon vehicle start-up. A record of several requests for traffic news following vehicle start-up may prompt the EAS 10 to gather such information upon vehicle start-up and ask the occupant 12 whether they would like to hear the local traffic. Other learned behaviors are also possible.

These learned requests, commands and/or preferences may be supplemented and/or initialized with occupant-defined criteria. For example, the occupant 12 may inform the EAS 10 that it does not like to discuss sports but does like to discuss music, etc. In this example, the EAS 10 may refrain from initiating conversations with the occupant 12 regarding sports but periodically talk with the occupant 12 about music.

Figure 2:
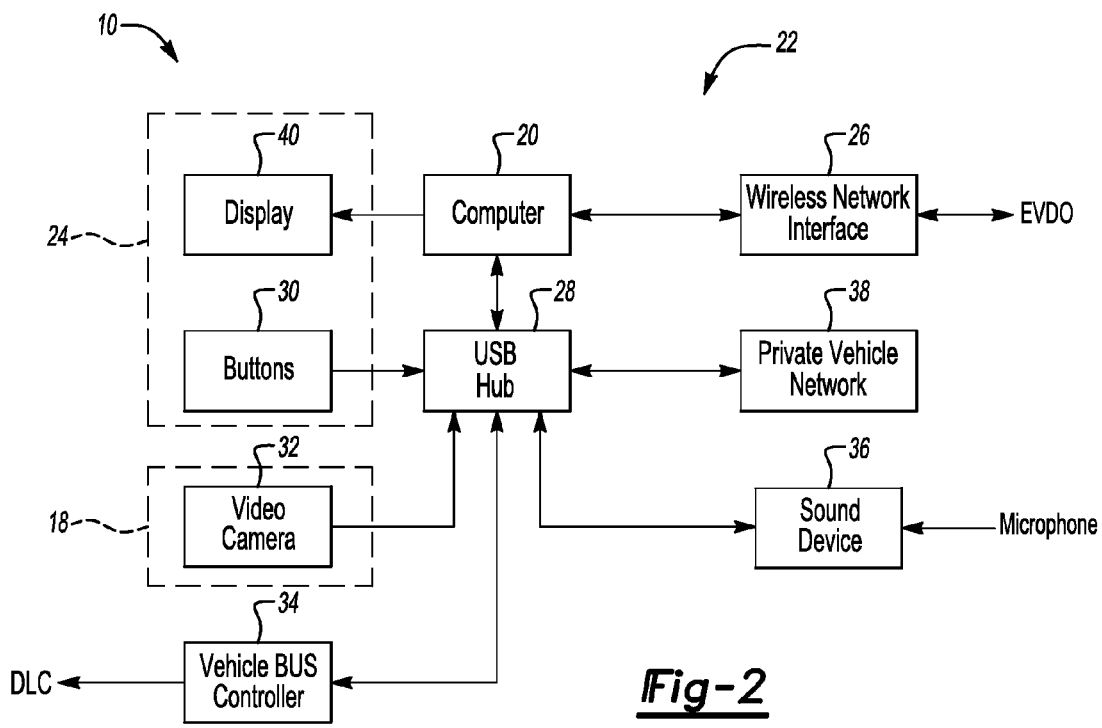
FIG. 2 is a block diagram of a portion of the emotive advisory system of FIG. 1.

Referring now to FIG. 2, the computer 20 communicates, bi-directionally, with (i) a wireless network interface 26 to reach the information sources 16*n* illustrated in FIG. 1 and (ii) a hub, e.g., a USB hub 28, to reach peripheral devices such as buttons 30, video camera 32, vehicle BUS controller 34, sound device 36 and a private vehicle network 38. The computer 20 also communicates with a display 40 on which, as explained above, an avatar may be rendered. Other configurations and arrangements are, of course, also possible.

Figure 3:
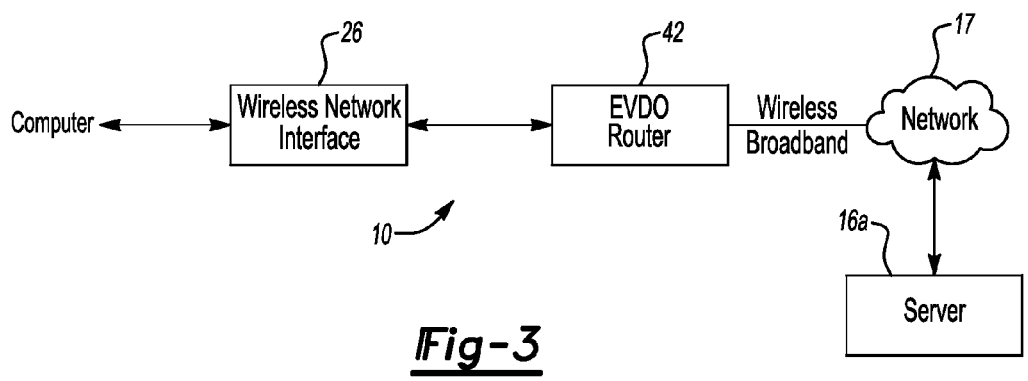
FIG. 3 is a block diagram of another portion of the emotive advisory system of FIG. 1.

Referring now to FIG. 3, the wireless network interface 26 may establish a communication link with the remote web server 16*a* via, for example, an Evolution-Data Optimized (EVDO) device 42 and the network 17, e.g., cellular broadband/Internet/etc. EVDO devices provide link-level, e.g., IEEE 802.1, packet data services over a cellular network. Information from the wireless network interface 26 is provided to the EVDO 42 and transmitted via Internet Protocol (IP) to a network (not shown) linked to the network 17. Transmission Control Protocol (TCP) and Universal Datagram Protocol (UDP) data packets are transported by the IP packets. Sockets are used to provide a connection-oriented (TCP) or connection-less (UDP) connection to the web server 16*a*. In other embodiments, any suitable wireless communication technique, such as Orthogonal Frequency Domain Multiplexed (OFDM), Metropolitan Area Network (MAN), WiMax, etc., may be used.

Figure 4:
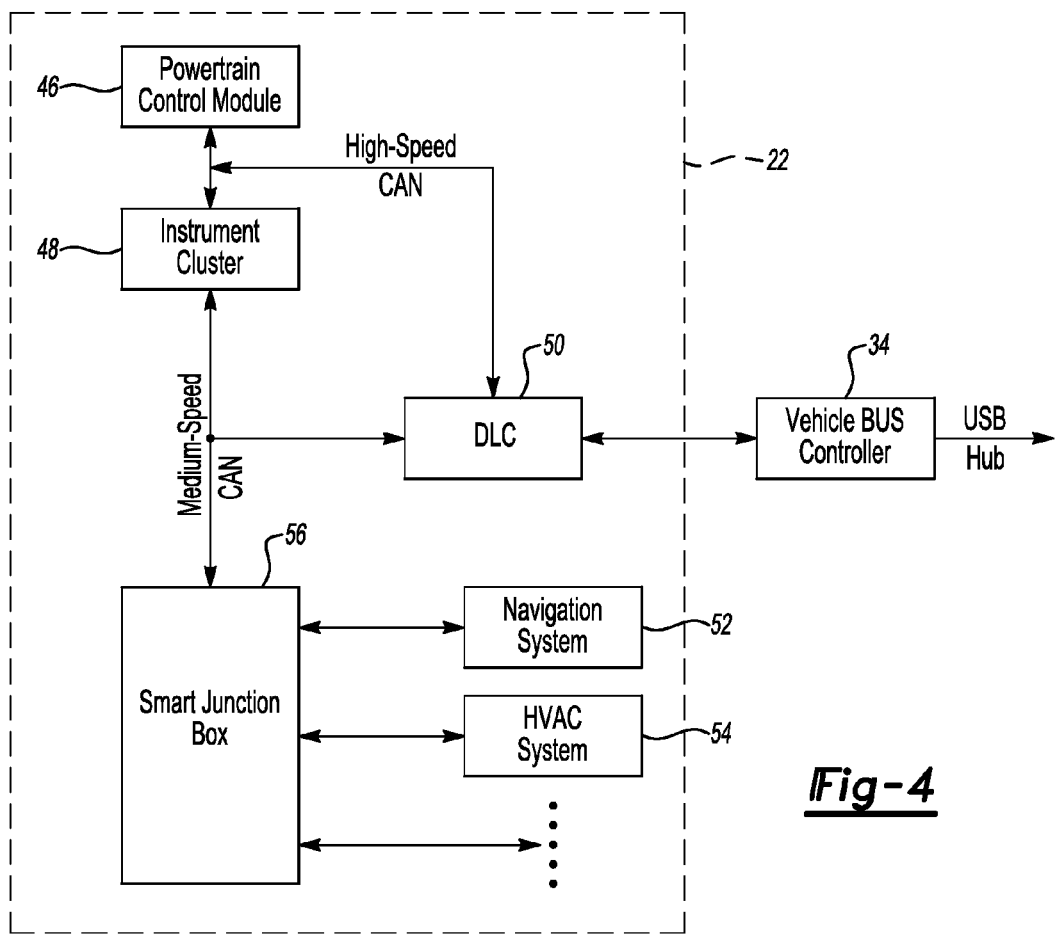
FIG. 4 is a block diagram of a portion of the automotive vehicle of FIG. 1.

Referring now to FIG. 4, the vehicle bus controller 34 may provide a port for the computer 20 illustrated in FIG. 2 to exchange information regarding the vehicle systems 22. The vehicle bus controller 34 of FIG. 4 exchanges information signals with, for example, a powertrain control module 46 and instrument cluster 48 via a Data Link Connector (DLC) 50. Similarly, the vehicle bus controller 34 may exchange information signals regarding a navigation system 52, HVAC system 54, etc. via a smart junction box 56 and the DLC 50. Such communication within a vehicle may be conducted via a Controller Area Network (CAN) bus, a Local Area Network bus or a Resistor Ladder Network (RLN) (also referred to as cascaded resistors). Any suitable communication technique, however, may be used.

Figure 5:
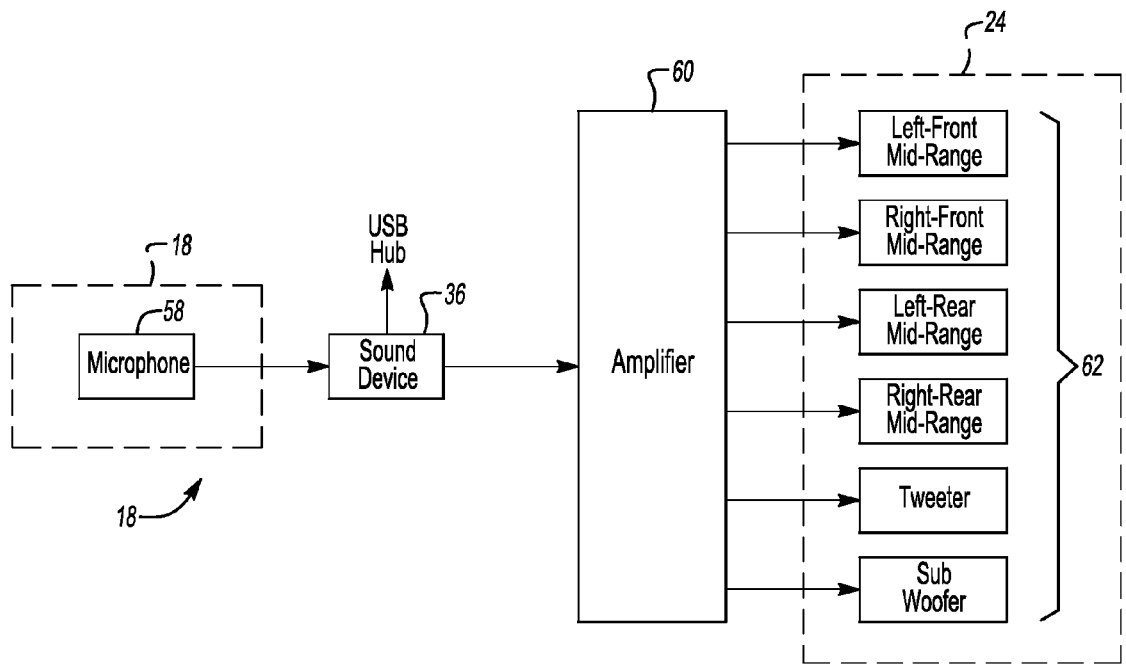
FIG. 5 is a block diagram of another portion of the automotive vehicle of FIG. 1.

Referring now to FIG. 5, the sound device 36 may receive analog audio inputs from a microphone 58. The sound device 36 converts the analog inputs to digital outputs for the computer 20 illustrated in FIG. 2. The sound device 36 may also receive digital inputs from the computer 20 representing, for example, the voice of the avatar. The sound device 36 converts the digital inputs to analog outputs for an amplifier 60. These amplified analog outputs may be played on a collection of speakers 62.

Figure 6:
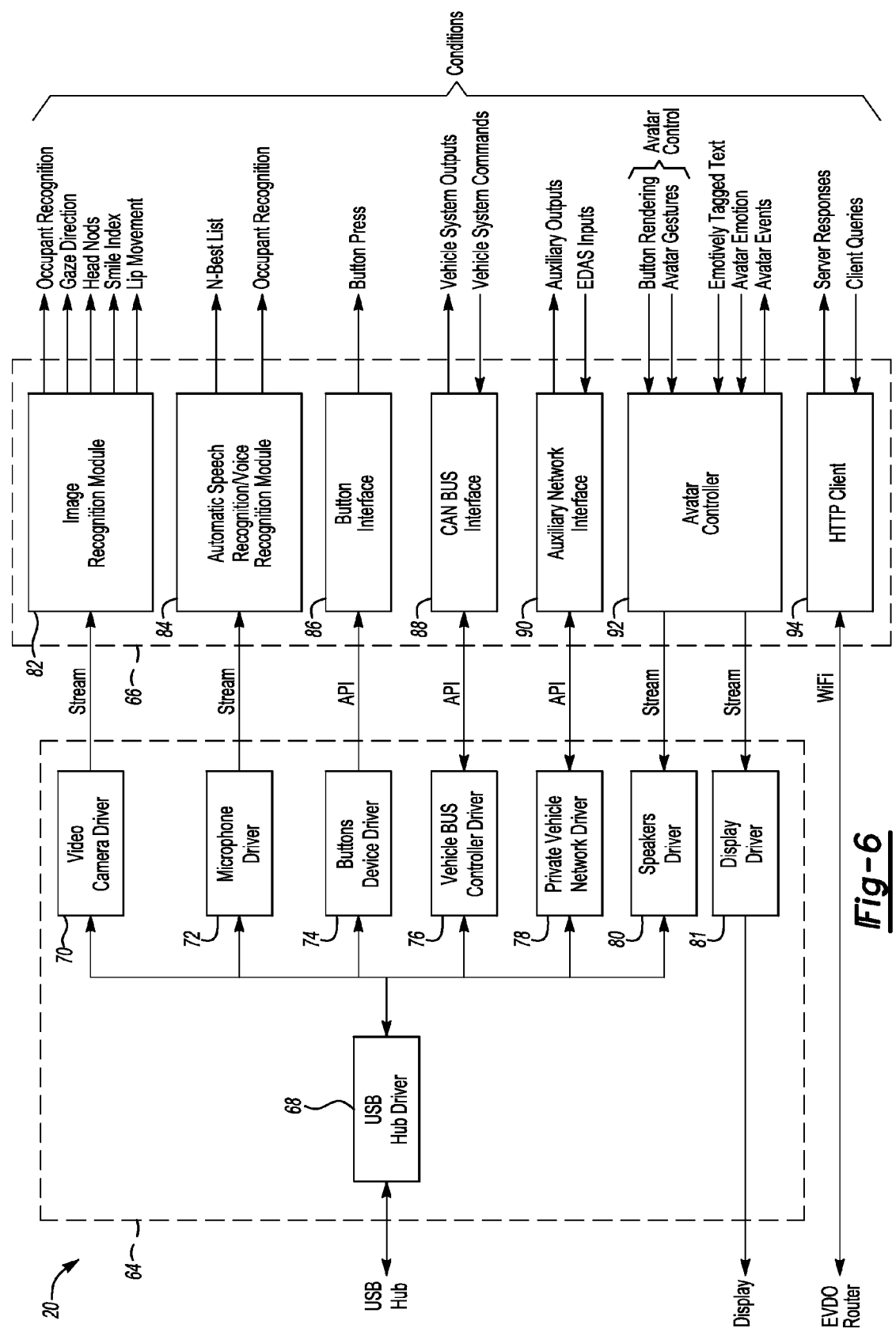
FIG. 6 is a block diagram of yet another portion of the emotive advisory system of FIG. 1.

Referring now to FIG. 6, the computer 20 may include device drivers 64 corresponding to certain hardware, such as the hardware illustrated in FIG. 2. The device drivers 64 interact with software modules 66 and as such, may provide an interface between the hardware illustrated in FIG. 2 and the software modules 66. The software modules 66 provide and/or receive outputs and/or inputs that, as discussed below, are used by a variety of subsystems within the EAS 10 illustrated in FIG. 1.

A peripheral interface bus, such as a USB hub driver 68, CAN bus, BLUETOOTH, etc., de-multiplexes/multiplexes information from/to the USB hub 28 illustrated in FIG. 2 for a video camera driver 70, microphone driver 72, buttons driver 74, vehicle bus controller driver 76, private vehicle network driver 78, speakers driver 80 and display driver 81. Of course, other and/or different drivers may be included as desired.

Several broad categories of networks may be used including ring, mesh, star, fully connected, line, tree and bus. USB is a hybrid star/tree network that operates at 1.5, 12, 480 and 4800 Mbit/second. The network may be wired or wireless, and commercial products are widely available that use industry standard chipsets such as the USB251x family of chips from SMSC Semiconductor. A USB implementation may have adequate throughput to support 6 audio channels, a video channel and various other devices. The network may be either wired or wireless. Other configurations are, of course, also possible.

The video camera driver 70 provides digital video data via an I/O stream to an image recognition module 82. The image recognition module 82 of FIG. 6 processes the digital video data and outputs parameters indicative of visual cues from the occupant 12 illustrated in FIG. 1. Parameters, of course, are mathematical abstractions of occupant features that may be tracked using suitable image recognition technique. These parameters may include occupant recognition, gaze direction, head nods, smile index, lip size and shape, pupil position, pupil size, nostril location, eyebrows, face profile, etc. Other parameters, such as scalp line and wrinkles, etc., may also be used.

Occupant recognition is a parameter that characterizes the identity of the occupant 12. The gaze direction, head nods, smile index and lip movement are parameters that characterize movements of the occupant 12.

In the embodiment of FIG. 6, the image recognition module 82 recognizes occupant features, tracks them from image to image and recognizes patterns of movement. These movements are then classified into particular gestures via a gesture classification algorithm, e.g., sequential vector machine, neural network, etc., resulting in the parameters indicative of visual cues from the occupant 12. In other embodiments, the image recognition module 82 may employ any suitable image recognition technique. Several such algorithms/methods are known in the art. One approach uses spectral graph techniques to cluster shape and appearance features, then groups the clusters into time-varying facial gestures. A second approach uses a classifier based on real-valued hyperplanes implemented on specialized hardware for rapid processing. A third method combines an Adaptive View-based Appearance Model (AVAM) with a 3D view registration algorithm. Other methods are also possible.

The microphone driver 72 provides audio via an I/O stream to an automatic speech recognition/voice recognition module 84. The automatic speech recognition/voice recognition module 84 of FIG. 6 processes digital audio data and outputs parameters indicative of audio cues from the occupant 12 illustrated in FIG. 1. In other embodiments, the automatic speech recognition/voice recognition module 84 may also process the one or more parameters, such as lip movement, output by the image recognition module 82. The parameters output by the automatic speech recognition/voice recognition module 84 include an N-Best list and occupant recognition. Any suitable parameters, however, may be used.

An N-Best list, in this example, may comprise an utterance recording, i.e., a sound recording, of a portion of speech from the occupant 12 illustrated in FIG. 1 and a set of associated recognition entries. Each recognition entry may include a textual version of the utterance recording along with a confidence parameter. The confidence parameter indicates the degree of confidence with which the text accurately captures the words associated with the utterance recording. Each recognition entry may also include a natural language version of the utterance recording. For example, the spoken sentence "The brown dog ran fast." may be represented in natural language as (((The(brown*(dog))) (fast*(ran))).

In the embodiment of FIG. 6, once audio data is received, phonological features are extracted from the digital data and sentence endpoints are identified using, for example, end pointing algorithms. Phonological features for each sentence are compared with a list of possible sentences as a hypothesis set. The hypotheses the system determines have the highest confidence of being the correct transcription of the phonological data are selected and placed in the N-best list along with a confidence level. An utterance recording for a particular sentence is recorded into an audio file which, as discussed below, may later be analyzed for emotional content. The automatic speech recognition/voice recognition module 84 also outputs a natural language version of the phonological features which contains syntactic information.

As discussed above, a particular utterance recording may result in several recognition entries. For example, if the occupant 12 illustrated in FIG. 1 says "get me the news," the automatic speech recognition/voice recognition module 84 may produce two hypothesis based only on the sound signal it receives: "get me the news" and "get me the reviews." The discourse context associated with dialog between the occupant 12 and the EAS 10 illustrated in FIG. 1 may be used to select between multiple hypotheses.

Discourse contextual analysis algorithms may be implemented by using the knowledge of the current topic to determine the appropriateness of a particular hypothesis. For example, a discussion regarding restaurants is not likely to involve a query about the news. As a result, a current discourse context may be used to reprioritize the N-best list, introducing context into the recognition confidence.

Within a particular context, such as "news" or "restaurants," a certain sub-set of recognizable sentences is more likely to occur than others. For example, the sentence "give me the news" may be more likely to occur in the "news" context while the sentence "give me the reviews" may be more likely to occur in the "restaurants" context. If an N-best list contains sentences from different contexts, the sentence from the current context may be assigned a higher recognition confidence, potentially reordering the N-best list.

The context may also be used to determine whether a particular utterance is addressed to the EAS 10 illustrated in FIG. 1 or whether it is addressed to other occupants (not shown) of the vehicle 14. For example, if the EAS 10 announces that fuel is low and requests driver input as to how to proceed, if the driver responds with "I am hungry," the EAS 10 may use context to help determine if the phrase "I am hungry" was addressed to the EAS 10. With the vehicle systems interface described above, it may first find if there are multiple occupants in the vehicle 14 by getting input from an Occupant Classification System (OCS). If there are multiple occupants, the EAS 10 may then assume that the out of context phrase "I am hungry" was part of a discussion with the other vehicle occupants rather than a request to find a restaurant directed to the EAS 10.

The identity of the speaker may be determined by combining voice recognition from an automatic speech recognition/voice recognition module discussed below, image recognition, e.g., lip movements, etc., and acoustics to determine the speaker's location, etc.

The occupant recognition parameter indicates whether the automatic speech recognition/voice recognition module 84 recognizes the voice of the occupant 12 illustrated in FIG. 1 and also to whom the voice belongs. In the embodiment of FIG. 6, the occupant recognition parameter is generated by comparing a sound recording captured from the occupant 12 with stored sound features associated with a known list of occupants. Any suitable voice recognition algorithm, however, may be used.

The buttons driver 74 provides digital information indicative of whether, for example, the buttons 30 illustrated in FIG. 2 are being pressed via an Application Programming Interface (API) to a button interface module 86. The button interface module 86 of FIG. 6 processes this information and outputs a parameter indicative of such button presses. The embodiment described here is multimodal in that pressing a button is equivalent to speaking a command, and alters the context of the discourse. Therefore, button pushes may be used to determine the occupant's location and identity, and may alter the selection of recognition hypothesis in the N-Best list.

The vehicle bus controller driver 76 provides, for example, CAN messages including a CAN I.D., a message type and 8 data bytes via an API to a CAN bus interface 88. Of course, any suitable vehicle network, e.g., flex ray, J-1850, etc., and associated protocol may be used. The CAN bus interface 88 processes these CAN messages and outputs protocol indicative of a state of a vehicle system, e.g., throttle position, wheel speed, fuel level, fuel consumption, transmission gear, brake torque, etc.

The CAN bus interface 88 also receives inputs from, as discussed below, agents in the form of EAS protocol. Any suitable protocol, however, may be used. The CAN bus interface 88 repackages these messages into CAN protocol and forwards them to the USB hub 28 illustrated in FIG. 2 via the drivers 68, 76. In some embodiments, these messages may include commands and/or operating parameters for the vehicle systems 22 illustrated in FIG. 4. For example, a message may include information as to how the powertrain control module 46 illustrated in FIG. 4 should control the engine (not shown). Other arrangements are also possible.

The private vehicle network driver 78 provides digital information associated with certain vehicle systems not in communication with the CAN illustrated in FIG. 4 to an auxiliary network interface 90 via an API. For example, window position and window motor voltage information may not be broadcast via the CAN but may be accessible through the private vehicle network driver 78. Additionally, devices installed on the private vehicle network may have analog/digital and digital/analog converters that allow the EAS 10 illustrated in FIG. 1 to ascertain the status of conventional controls connected to an RLN and also to take control of an RLN network to emulate the use of conventional controls.

The auxiliary network interface 90 of FIG. 6 obtains analog signals and converts them into a digital protocol. The auxiliary network interface 90 then converts the digital protocol into EAS protocol for use by certain EAS agents discussed in further detail below. Such information may be indicative of a state of the vehicle systems not in communication with the CAN illustrated in FIG. 4.

Similar to the CAN bus interface 88, the auxiliary network interface 90 also receives inputs from certain EAS agents in the form of EAS protocol. The auxiliary network interface 90 repackages these messages into a format for a digital to analog conversion. Analog outputs may then be delivered to, for example, the actuators 24 illustrated in FIG. 1 and/or various RLNs (not shown) within the vehicle 14 illustrated in FIG. 1.

An avatar controller 92, in the embodiment of FIG. 6, may be a computer program and rendering engine that supports rendering of the avatar on the display 40 illustrated in FIG. 2 using one of several sets of Application Programming Interfaces (API). Many rendering engines may be used for this purpose, including Renderware, Torque Game Engine, TV3D, 3D Game Studio, C4 Engine, DX Studio, Crystal Space, Game Blender, etc. These use several graphics oriented APIs including Direct3D, OpenGL, DirectX, SDL, OpenAL, etc.

The avatar controller 92 receives numerical as well as textual inputs to control geometric transformations of the avatar and its synthesized textual outputs. In the embodiment of FIG. 6, these inputs include parameters indicative of button rendering, avatar emotion, text-to-speech control and emotively tagged text. Other and/or different inputs may also be used.

The button rendering parameter informs the avatar controller 92 as to how to render any virtual buttons visible from the display 40 illustrated in FIG. 2. The avatar gestures and text-to-speech control inform the avatar controller 92 as to how to render movement and facial expressions of the avatar as the avatar speaks. For example, the avatar gestures may control hand movements, gaze direction, etc., of the avatar. The text-to-speech control may control when to begin, end, suspend, abort or resume any text-to-speech operations. The avatar emotion and emotively tagged text, as discussed in detail below, inform the avatar controller 92 as to how to render movement and facial expressions of the avatar as the avatar expresses emotion.

Briefly, avatar emotion in the embodiment of FIG. 6 includes weighted vector representations of a set of emotions for the avatar. Emotively tagged text includes marked-up phrases that indicate emotional content associated with certain words of the phrase. The avatar appearance is dynamically altered to express emotion, indicate speech is taking place and/or convey information, etc. The avatar expression is controlled by manipulating specific points on the surface of the avatar. In a computer generated avatar, a mathematical representation of a 3D surface of a physical avatar is made, typically using polygonal modeling techniques/algorithms. Alternatively, the surface may be modeled using spline curves (such as NURBS), subdivision surfaces, equation based representations, etc. In polygonal modeling the approach is to approximate the real surface with many conforming flat polygons. Each polygon may be associated with color(s) and a texture map that defines such optical characteristics as surface roughness, color variation, reflectivity, specularity, etc. The model may then be illuminated using a shading algorithm that assumes a distribution of point light sources and ambient light. Shading methods generally trade off rendering speed against how natural the image looks, and several methods are known in the art such as ray tracing, Nebulaud shading, Gouraud Shading, Phong shading, Cel-shading, etc. In some embodiments, the naturalness of the shading should match the naturalness of the voice and the phraseology of the avatar. The appearance of the avatar may be dynamically manipulated by moving the position of the polygon vertices, changing the color and texture of polygons, changing the color and position of the lights, etc. in the rendering engine.

The avatar controller 92 processes the above described inputs and provides image frames, via a stream, to the display driver 81. The display driver 81 processes the image frames using any suitable technique and outputs them to the display 40 illustrated in FIG. 2.

The avatar controller 92 also provides digital audio data associated with the above inputs to the speakers driver 80 via an I/O stream. The speakers driver 80 provides this data to the USB hub driver 68 for delivery to the sound device 36 illustrated in FIG. 5.

The avatar controller 92 generates several outputs that, as explained below, may be used as timing information to facilitate control of the avatar. In the embodiment of FIG. 6, the avatar controller 92 outputs parameters indicative of a completed text string, sentence, word, syllable, viseme, gesture, etc. by the avatar (collectively referred to herein as avatar events.) Of course, other and/or different parameters may be used. Whether the avatar has completed a textual string and the current lip position of the avatar may be used to determine whether and/or when to interrupt the avatar's current speech with, for example, speech of a more urgent nature.

The lip movements of the avatar may be animated using a set of predefined lip positions that are correlated to each allophone of speech. A number corresponding to a viseme may be used to index each position which is either morphed or concatenated to the rest of the avatar's face. There are standard viseme sets such as the Disney visemes and several others that are in common use. The text-to-speech engine produces a stream of visemes that are time synchronized to the speech that is produced. The visemes are streamed to the rendering engine to affect lip movement.

In the embodiment of FIG. 6, an HTTP client 94 may establish an inter-process socket connection with one of the remote servers 16n illustrated in FIG. 1. The HTTP client 94 forms an HTTP URL, sends it through the socket connection to the remote server 16n and waits for a response. The remote server 16n formats a response, for example, in XML and sends the response through the socket connection to the HTTP client 94. The HTTP client 94 may then reformat the response into, for example, EAS protocol for use by an EAS agent.

As described herein, the EAS 10 illustrated in FIG. 1 and other related systems include a number of hardware and/or software modules that communicate with each other through, for example, inter-process communication. For clarity, techniques that may be used to facilitate such communication are described with reference to FIGS. 7 and 8 rather than addressing such communication issues in detail when discussing other Figures provided herein. Other suitable communication architectures, however, may also be used.

Figure 7:
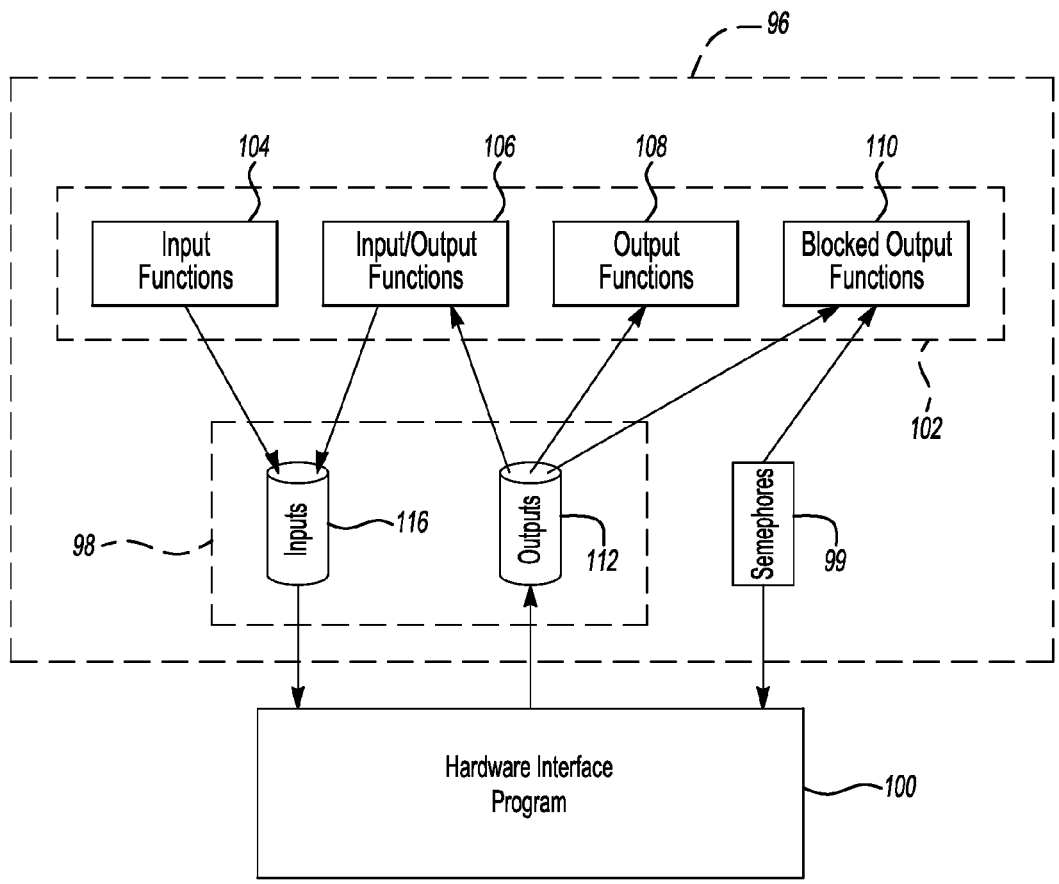
FIG. 7 is a block diagram of an embodiment of a communications manager for the emotive advisory system of FIG. 1.

Referring now to FIG. 7, an embodiment of a communications manager 96, such as a message oriented middleware solution (MOM), e.g., SunJava, Java message service, advanced message queuing protocol, etc., includes a set of databases 98 and a set of semaphores 99 that permit a hardware interface program 100 to broadcast/receive information to/from modules of the EAS 10 illustrated herein. Transactions to/from the databases 98 may be atomic and may be synchronized using the semaphores 99.

In certain embodiments, some of the software modules 66 described in FIG. 6 and elsewhere herein may each implement the communications model of FIG. 7. For example, the hardware interface program 100 may represent the image recognition module 82, the button interface 86, etc., illustrated in FIG. 6.

In the embodiment of FIG. 7, software modules 102 are logically grouped into several categories: input functions 104, input/output functions 106, output functions 108 and blocked output functions 110. As apparent to those of ordinary skill, the software modules 102 implement the transactions to/from the databases 98 using any suitable I/O functions, and convert any hardware protocol, e.g., CAN messages, etc., into, for example, EAS protocol, XML, etc.

Data from the hardware interface program 100 to be processed by any of the software modules 102 is stored in one or more of the databases 98. Output data from the hardware interface program 100 for the input/output functions 106, output functions 108 and blocked output functions 110 is stored in an outputs database 112 and accessed by these functions as necessary. Output data from the hardware interface program 100 for the blocked output functions 110 is stored in the semaphores database 99 and, similar to above, accessed by the blocked output functions 110 as necessary.

Data from the software modules 102 to be processed by the hardware interface program 100 is likewise stored in the databases 98. Input data from the input functions 104 and input/output functions 106 is stored in an inputs database 116 and accessed by the hardware interface program 100 as necessary.

As apparent to those of ordinary skill, the communications manager 96 of FIG. 7 is logically arranged so as to separate the time base of the hardware interface program 100 and the software modules 102. The distributed databases 98 are the intermediaries that permit the hardware interface program 100 and software modules 102 to each operate within their own timing constraints. This separation may promote scalability between software and hardware comprising the EAS 10 illustrated in FIG. 1.

Figure 8:
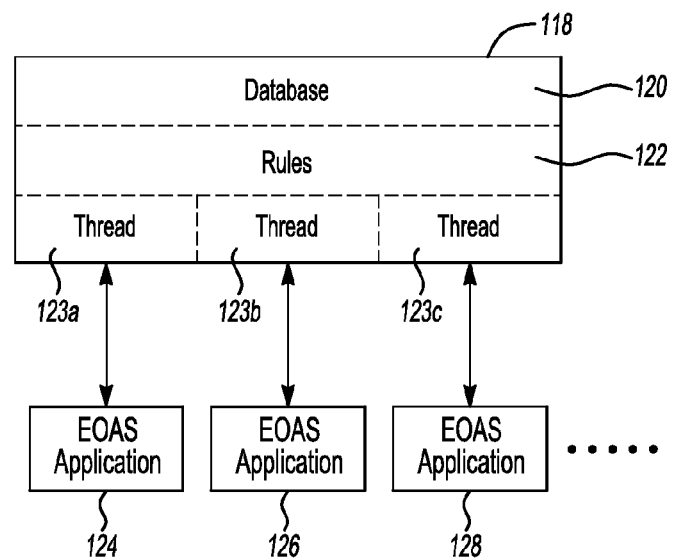
FIG. 8 is a block diagram of another embodiment of a communications manager for the emotive advisory system of FIG. 1.

Referring now to FIG. 8, another embodiment of a communications manager 118, e.g., an intelligent cross-bar system, etc., includes a centralized database 120 that logically interfaces with a set of rules 122. The rules 122 govern how data is to be written to and retrieved from the database 120 by various EAS application threads 123n (123a, 123b, 123c, etc.) associated with various EAS applications 124, 126, 128, etc. In this example, the EAS application 124 may represent one or more of the software modules 66 illustrated in FIG. 6 and elsewhere herein. The EAS application 126 may represent another one or more of the software modules illustrated in FIG. 6 and elsewhere herein, etc.

Threads 123n are established with the EAS applications 124, 126, 128, etc., when communication of data between them is required. For example, the communications manager 118 may establish a thread 123*a* with the EAS application 124 to permit it to write data to the database 120 that will be later used by the EAS application 126.

The data is assembled into protocol and communicated via a socket between the EAS application 124 and the communications manager 118. The rules 122 parse the data and assign it to its appropriate location in the database 120 depending upon, for example, the nature of the data and which application produced the data. An appropriate set of other threads 123*n* are then invoked to transmit the data via, for example, the EAS protocol to their associated application. For example, a thread 123*b* is established to facilitate the communication between the EAS application 126 and the communications manager 118.

The EAS application 126 submits a request, via a socket, for the data. The rules 122 parse the request and provide the requested data thread 123*b* and thus the EAS application 126 via the socket.

As mentioned above, the avatar may convey information to the occupant 12 illustrated in FIG. 1 and/or facilitate spoken dialog with the occupant 12 through the use of simulated emotion. This simulated emotion may be expressed visually by the avatar and/or audibly, for example, by the speakers 62 illustrated in FIG. 5. Techniques to generate simulated emotion are described with reference to FIGS. 9A and 9B.

Figure 9A:
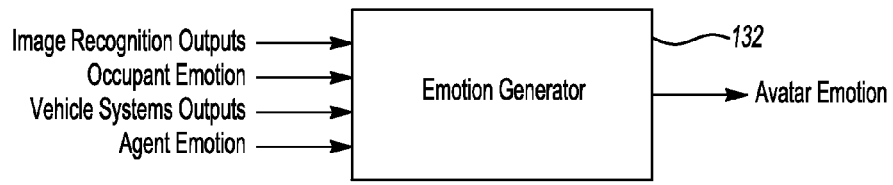
FIGS. 9A and 9B are block diagrams of portions of an emotional engine for the emotive advisory system of FIG. 1.

Referring now to FIG. 9A, an emotion generator 132 receives a collection of inputs from various modules described herein, analyzes/transforms them and produces a simulated emotional state for the avatar. This simulated emotional state, in the embodiment of FIG. 9A, is in the form of a weighted emotional vector.

The simulated emotional state is communicated to and rendered by the avatar controller 92 illustrated in FIG. 6. As discussed below, the relative weighting of each variable of the emotional vector instructs the avatar controller 92 as to the manner in which the avatar should appear and speak to express the appropriate emotion(s).

In the embodiment of FIG. 9A, the emotion generator 132 is implemented in software. The emotion generator 132, however, may be implemented in firmware or any other suitable configuration.

An emotion, such as fear, may be associated with a particular set of avatar facial positions and speech patterns/tones that would be recognized as an expression of fear. Returning again to FIG. 6, the avatar controller 92 transforms the emotional vector, i.e., avatar emotion, generated by the emotion generator 132 illustrated in FIG. 9A into a set of movements and facial expressions indicative of the emotion(s) to be expressed. The avatar controller 92, for example, may include a database that transforms, e.g., maps, the range of weighted values for each emotion with a set of corresponding facial expressions: an avatar emotion of "happy" may correspond to lip positions indicative of a smile; an avatar emotion of "happy" and "surprised" may correspond to lip positions indicative of a smile and eyebrow positions that are raised. The degree to which the avatar is smiling and/or raising its eyebrows, in this example, is a function of the weighting variable associated with the emotion. The more heavily weighted the "surprised" emotion, the higher the eyebrow position, etc. For example, if the emotional vector is weighted to 50% "surprise," and 50% "fear," the avatar will appear (and speak) in a manner that suggests it is surprised and afraid.

Several systems and/or algorithms may be used to determine the correspondence between facial expressions and emotions. For example, there is a long tradition of fine art that has codified the relationship between expression and emotion. In addition there are codifications that correspond to a scientific approach such as the Facial Action Coding System. Animators have developed a variety of packaged systems for putting emotion into pre-rendered animated characters such as the Facial Animation Tools et for Maya and the Intel Facial Animation Library. The relationship between different emotions, however, may be more complex. "Fear," for example, activates specific sets of muscles in the face, as does "surprise." To the extent the two sets are separate, the motions they produce are separate. Two emotions, however, may activate the same muscles and, to the extent this is the case, those motions may be compromised/blended.

Figure 9B:
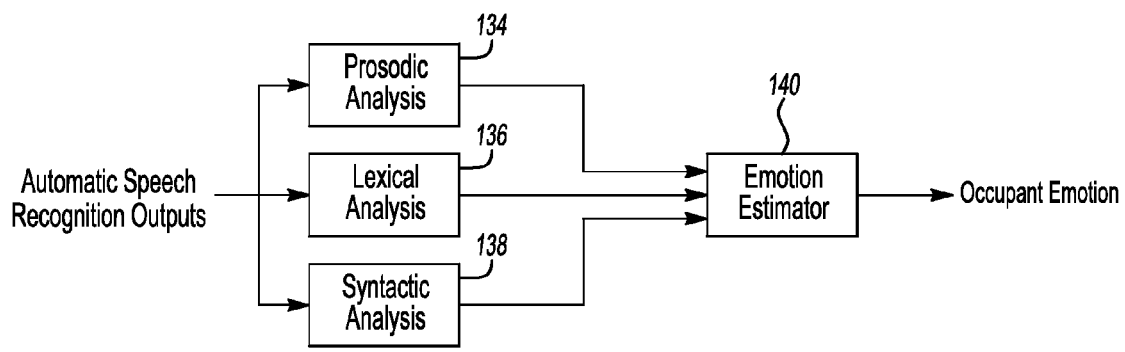

Referring now to FIG. 9B, the outputs of the automatic speech recognition/voice recognition module 84 illustrated in FIG. 6 may be pre-processed by one or more of a prosodic analysis module 134, lexical analysis module 136 and/or syntactic analysis module 138. The outputs of the modules 134, 136, 138 are provided to an emotion estimator module 140. The emotion estimator module 140 aggregates these outputs to produce an estimation of the emotional state of the occupant 12 illustrated in FIG. 1. In the embodiment of FIG. 9B, the modules 134, 136, 138, 140 are implemented in software. These modules, however, may be implemented in any suitable fashion.

The prosodic analysis module 134 of FIG. 9B may use multi-parametric speech analysis algorithms to determine the occupant's affective state. For example, the specific features of the speech input, such as speech rate, pitch, pitch change rate, pitch variation, Teager energy operator, intensity, intensity change, articulation, phonology, voice quality, harmonics to noise ratio, or other speech characteristics, are computed. The change in these values compared with baseline values is used as input into a classifier algorithm which determines the emotion on either a continuous scale or as speech categories.

Prosodic analysis algorithms may be made more powerful if combined with semantic analysis. These algorithms analyze the prosody of the occupant's speech. For example, a rule may be implemented that maps a volume of speech with the emotion "excitement": The greater the volume, the higher the rating of "excitement." Other rules, of course, may also be implemented. Basic emotions may include "fear," "anger," "sadness," "happiness" and "disgust." Voice factors that may be indicative of these emotions may include speech rate, average pitch, pitch range, intensity, timbre and articulation.

Lexical analysis of the speech may also be helpful: use of a word such as "overcast" when "cloudy" would be more common could indicate a negative emotion. Further, syntax may be analyzed to determine, for example, if the speaker uses the passive or active voice. Use of the active voice may indicate confidence and happiness. Other techniques and/or algorithms, etc., however, are also possible.

The lexical and syntactic analysis modules 136, 138 each apply a set of algorithms implemented, in certain embodiments, as rules to the speech recognition outputs to generate respective emotional vectors indicative of an assessed emotional state of the occupant 12 illustrated in FIG. 1. Lexical analysis algorithms may extract the text form of the words uttered by the occupant and classify them using an affective lexicon. One such lexicon is the Dictionary of Affective Language (DAL) that contains words of unambiguous emotional content. Statistical analysis may be applied to all the words in a corpus with unambiguous emotional content to determine the emotion the speaker wishes to express. For example, the lexical analysis module 136 may map the frequency of the use of expletives by the occupant 12 with the emotion "frustration": The greater the frequency, the higher the rating of "frustration."Algorithms implemented, in certain embodiments, as rules in the syntactic analysis module 138 may map an average word length of spoken sentences with the emotion "anger": the shorter the average sentence, the higher the rating of "anger." Other algorithms and/or rules, etc. may also be implemented. Syntactic analysis algorithms may use factors in the spoken speech such as sentence length, use of punctuation, verb class (experience or action), verb evaluation (positive or negative), verb potency (high or low), etc. to determine the emotion of the speaker.

In certain embodiments discussed herein, four emotions are used to represent the assessed emotional state of the occupant 12 illustrated in FIG. 1: "happy," "sad," "fear" and "surprise." Other and/or different emotions, however, may be used. These four emotions may be represented by three variables: "HS," "FR," and "SP." The "HS" variable, for example, may take on the values negative high ("NH"), negative low ("NL"), neutral ("NT"), positive low ("PL") and positive high ("PH"). "NH" and "NL" are indicative of the degree of "sad." "PL" and "PH" are indicative of the degree of "happy." The "FR" and "SP" variables may each take on the values neutral (NT), positive low (PL) and positive high (PH).

The emotion estimator 140 of FIG. 9B applies algorithms implemented as a set of rules to the emotional vectors output by the modules 134, 136, 138 and transforms them into an estimate of the emotion of the occupant 12 illustrated in FIG. 1. Other suitable algorithms and/or analytical techniques, such as neural networks, may also be used. A set of fuzzy based rules, for example, may be applied to each of the modules 134, 136, 138 assessment of "fear," i.e., the "FR" variable, to reach an aggregate measure of "fear." For example, if the respective measures of "fear" from each of the modules 134, 136, 138 are "HP," "LP" and "NT," then the fuzzy rules applied by the emotion estimator 140 may yield an aggregate measure of "fear" for the occupant 12 as "LP." The measure of "fear" from each of the modules 134, 136, 138, in this example, is thus effectively equally weighted.

In some embodiments, the algorithms applied by the emotion estimator 140 may bias the results in favor of certain of the modules 134, 136, 138 depending upon, for example, the accuracy and precision with which each measures the emotional state of the occupant 12. In other embodiments, the emotion estimator 140 may dynamically bias the results in favor of certain of the modules 134, 136, 138 based upon feedback from the occupant 12 illustrated in FIG. 1. The EAS 10 illustrated in FIG. 1 may, for example, occasionally ask the occupant 12 to describe their emotional state in terms of "happy," "sad," "fear" and "surprise." Upon receiving such feedback from the occupant 12, the emotion generator 140 may be tuned so that its results more closely track the occupant's own assessment of their emotional state. If, for example, the lexical analysis module 136 is producing an assessed emotional state that most closely resembles the occupant's own assessment of their emotional state, the emotion generator 140 may begin to ignore or rely less on the emotional assessments from the prosodic and syntactic modules 134, 138.

Similar evaluations to those discussed above may be performed for other variables of the emotional vectors from each of the modules 134, 136, 138. Collectively, these variables form an emotional vector that represents an estimated occupant emotional state based upon the speech of the occupant 12 illustrated in FIG. 1. As discussed below, this estimated occupant emotional state may be used as an input in determining the appropriate simulated emotional state for the avatar.

Returning again to FIG. 9A, occupant emotion from the emotion estimator 140 illustrated in FIG. 9B, image recognition outputs from the image recognition module 82 illustrated in FIG. 6, vehicle systems outputs from the CAN bus interface 88 illustrated in FIG. 6 and agent emotion may be provided as inputs to the emotion generator 132.

As discussed in more detail below, agents may be independent programs that interact with the EAS 10 illustrated in FIG. 1 to implement specific tasks/functions. In the embodiment of FIG. 9A, agent emotion may be output by the agent(s) and indicate the quality with which the agent(s) is executing a task or an issue with the state of the vehicle 14 illustrated in FIG. 1. For example, if the engine (not shown) is low on oil, the avatar may reflect this with a negative expression. Likewise, a web agent that is responsible for establishing and maintaining a wireless communication link with remote locations may output an emotion that is a measure of the connectivity and performance associated with the communication link.

The following is an example algorithm implemented as a set of rules for transforming the connectivity and performance associated with the web agent discussed above into a set of emotions. As apparent to those of ordinary skill, this example may also be illustrative of other types of algorithms discussed herein. In this example, the connectivity ("Conn") of the computer 20 illustrated in FIG. 1 with information sources accessible via the remote network 17 illustrated in FIG. 1 is characterized as either "Poor" or "Good." The performance ("Perf") associated with the connectivity is characterized as "Low," "Medium" or "High." Changes in the connectivity ("ConnChng") and performance ("PerfChng") are characterized as positive ("Pos"), neutral ("Zero") or negative ("Neg"):

1. If (Conn is Poor) and (ConnChng is Pos) then (HS is NL) (FR is PL) (SP is PL).
2. If (Conn is Poor) and (ConnChng is Zero) and (Perf is Low) and (PerfChng is Zero) then (HS is NL) (FR is PL) (SP is NT).
3. If (Conn is Good) and (ConnChng is Zero) and (Perf is Low) and (PerfChng is Neg) then (HS is NL) (FR is PL) (SP is NT).
4. If (Conn is Good) and (ConnChng is Zero) and (Perf is Low) and (PerfChng is Zero) then (HS is NL) (FR is PL) (SP is NT).
5. If (Conn is Good) and (ConnChng is Zero) and (Perf is Low) and (PerfChng is Pos) then (HS is NT) (FR is NT) (SP is NT).
6. If (Conn is Good) and (ConnChng is Zero) and (Perf is Medium) and (PerfChng is Neg) then (HS is NT) (FR is NT) (SP is NT).
7. If (Conn is Good) and (ConnChng is Zero) and (Perf is Medium) and (PerfChng is Zero) then (HS is PH) (FR is NT) (SP is NT).
8. If (Conn is Good) and (ConnChng is Zero) and (Perf is Medium) and (PerfChng is Pos) then (HS is PL) (FR is NT) (SP is NT).
9. If (Conn is Good) and (ConnChng is Zero) and (Perf is High) and (PerfChng is Zero) then (HS is PL) (FR is NT) (SP is NT).

10. If (Conn is Good) and (ConnChng is Zero) and (Perf is High) and (PerfChng is Pos) then (HS is PL) (FR is NT) (SP is NT).
11. If (Conn is Good) and (ConnChng is Neg) and (Perf is Low) and (PerfChng is Neg) then (HS is NL) (FR is PL) (SP is NT).
12. If (Conn is Good) and (ConnChng is Neg) and (Perf is Low) and (PerfChng is Zero) then (HS is NT) (FR is PL) (SP is NT).
13. If (Conn is Good) and (ConnChng is Neg) and (Perf is Low) and (PerfChng is Pos) then (HS is NT) (FR is NT) (SP is NT).
14. If (Conn is Good) and (ConnChng is Neg) and (Perf is Medium) and (PerfChng is Neg) then (HS is NT) (FR is NT) (SP is PL).
15. If (Conn is Good) and (ConnChng is Neg) and (Perf is Medium) and (PerfChng is Zero) then (HS is PL) (FR is NT) (SP is PL).
16. If (Conn is Good) and (ConnChng is Neg) and (Perf is Medium) and (PerfChng is Pos) then (HS is PL) (FR is NT) (SP is NT).
17. If (Conn is Good) and (ConnChng is Neg) and (Perf is High) and (PerfChng is Neg) then (HS is PL) (FR is PL) (SP is PL).
18. If (Conn is Good) and (ConnChng is Neg) and (Perf is High) and (PerfChng is Zero) then (HS is PL) (FR is PL) (SP is NT).
19. If (Conn is Good) and (ConnChng is Neg) and (Perf is High) and (PerfChng is Pos) then (HS is PL) (FR is NT) (SP is PL).

The first rule indicates that if the connectivity is poor and the change in connectivity is positive, then "happy/unhappy" is low negative, "fear" is low positive and "surprise" is low positive. The other rules may be interpreted in a similar fashion.

One or more of the above inputs may be used by the emotion generator 132 to generate the avatar emotion. As an example, the emotion generator 132 may ignore all but the vehicle systems outputs during vehicle operation so that the emotion expressed by the avatar is effectively a vehicle gauge. A parameter indicative of a position of an accelerator pedal of the vehicle 14 illustrated in FIG. 1 may, for example, be mapped with an eyebrow angle of the avatar. When accelerating, the avatar may display an aggressive expression with its eyebrows angled down. When decelerating, the avatar may display a relaxed expression with its eyebrows angled up. Similarly, available power to the occupant 12 illustrated in FIG. 1 may be mapped with a mouth curvature of the avatar. When the available power is greater than the requested power, the avatar may display a happy expression with its mouth showing a smile. When the available power is less than the requested power, the avatar may display an unhappy expression with its mouth showing a frown. Other configurations are, of course, also possible. As another example, the emotion generator 132 may ignore all but the speech and image recognition outputs if, for example, a non-driver occupant (not shown) is engaged in a conversation with the avatar. In this example configuration, the avatar does not convey vehicle related information to the non-driver occupant. Other configurations and arrangements are also possible.

This selective capability of the emotion generator 132 may reflect motivation and intent on the part of the EAS 10 illustrated in FIG. 1. For example, the EAS 10 may use simulated emotion to convey the urgency of what is being said, to appeal to the occupant's emotions, to convey the state of the vehicle systems 22 illustrated in FIG. 1, etc. The EAS 10 may thus determine the appropriate times to display emotions indicative of various inputs.

The selective capability discussed above may be implemented through occupant request and/or automatically. In some embodiments, the occupant 12 illustrated in FIG. 1 may instruct the EAS 10 to ignore all but vehicle information, e.g., vehicle systems outputs, (or other inputs illustrated in FIG. 9A) when generating its emotion. In other embodiments, the EAS 10 may automatically ignore all but vehicle information during vehicle operation if, for example, the EAS 10 intends to emphasize the state of the vehicle 14 illustrated in FIG. 1 while communicating with the occupant 12. Algorithms may direct the EAS 10 to do this if, for example, certain vehicle operating parameters, such as tire pressure, fuel levels, engine temperature, etc., reach critical levels. Such an algorithm may provide that if the engine temperature is "hot", ignore all but vehicle systems outputs. In still other embodiments, the EAS 10 may automatically ignore all but the image recognition outputs and occupant emotion if, for example, the EAS encounters a new driver and is attempting to establish an emotional bond with this new driver. Other arrangements are also possible.

The emotion generator 132 may apply one or more algorithms, implemented in the embodiment of FIG. 9A, as a set of rules, similar to those discussed with reference to the emotion estimator 140 illustrated in FIG. 9B, to aggregate the inputs and generate the simulated emotional state for the avatar, i.e., avatar emotion. This emotional state takes the form of a weighted multi-variable vector, i.e., emotional vector. As discussed above, this emotional vector may include variables indicative of the emotions "happy," "sad," "surprise" and "fear" ("excitement-quiescence," "pleasant-unpleasant," etc.) Each variable may include an associated weighting value to indicate the degree with which that particular emotion is to be expressed. As discussed above, however, other techniques may be used to produce the emotional state for the avatar. For example, a suitable neural network may be provided that aggregates the various inputs received by the emotional generator 132 into the simulated emotional state of the avatar.

As discussed above, the EAS 10 illustrated in FIG. 1 may engage in conversation with the occupant 12 also illustrated in FIG. 1 to gather information from the occupant 12 and/or provide information to the occupant 12. Algorithms/techniques/methods used to manage and facilitate this conversation are discussed with reference to FIGS. 10 though 12.

Figure 10:
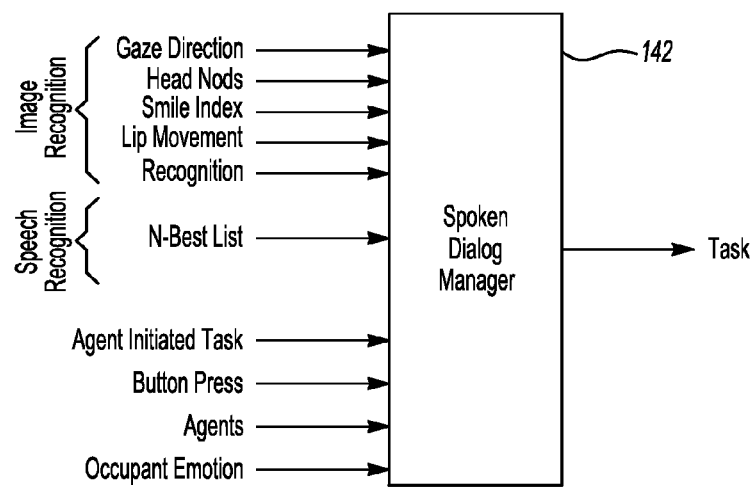
FIG. 10 is a block diagram of a spoken dialog manager for the emotive advisory system of FIG. 1.

Referring now to FIG. 10, a spoken dialog manager 142 receives inputs originating with the occupant 12 illustrated in FIG. 1, e.g., image recognition, speech recognition, button press, occupant emotion, as well as inputs originating with agents, e.g., agent initiated tasks. The spoken dialog manager 142 processes these inputs and generates tasks, for example, for the avatar, agents and/or vehicle systems 22 illustrated in FIG. 4.

The spoken dialog manager 142 of FIG. 10 may be implemented as software using a logic programming language such as PROLOG, Datalog, HiLog, λProlog, etc. These languages may be associated with computational linguistics. Of course, other high level languages, such as Java, LISP, etc., may also be used. In other embodiments, the spoken dialog manager 142 may be implemented on embedded processors, field programmable gate arrays, web-servers, etc.

The tasks generated by the spoken dialog system 142 may comprise text for the avatar to speak, the meaning the spoken dialog manager 142 wishes to convey, an event that will trigger text to be spoken, a priority for a given text to be spoken, the nature of how a current avatar operation should be interrupted (conveying urgency to the occupant), an emotion, an action for an agent, a priority for an action and an event that will trigger the execution of an action, etc.

The spoken dialog system 142 may generate content for a particular task based upon algorithms, implemented in the embodiment of FIG. 10, as a series of rules used to interpret the occupant and/or agent input within the given context. For example, a rule may provide that a downward gaze of at least 20 seconds will result in a task being generated that will remind the driver to keep their eyes on the road. The text and priority associated with such a task may be "Keep your eyes on the road!" and "High" respectively. The high priority of the task will cause the avatar to interrupt between words, for example, and abort any current task to convey the urgency needed to ensure the occupant is alerted. In this example, the task does not include an action for an agent as no agents are involved in the execution of this task. The task also does not include a triggering event because the task is intended to be performed immediately. Another rule may provide that a request from the occupant to "Put the vehicle in fuel economy mode." will result in a task being generated that will alter the appropriate engine tuning parameters to make the engine more fuel efficient. Assuming that such altering of engine tuning parameters must take place while the engine (not shown) is idling, the text and priority associated with such a task may be "I am putting the engine in fuel economy mode." and "Medium" respectively. The action may be directed to a powertrain agent and will include the appropriate instructions that will permit the agent to alter the desired parameters. The triggering event may be the engine at idle for at least 3 seconds. Still yet another rule may provide that any agent initiated task, discussed in more detail below, will result in a task being generated that will ask the occupant 12 illustrated in FIG. 1 whether it is acceptable to perform the task if the occupant emotion is "unhappy." The text and priority associated with such a task may be "I don't want to bother you, but the X agent recommends that I do Y. Is that O.K.?" and "Low" respectively. Other and/or different rules may also be implemented.

Figure 11:
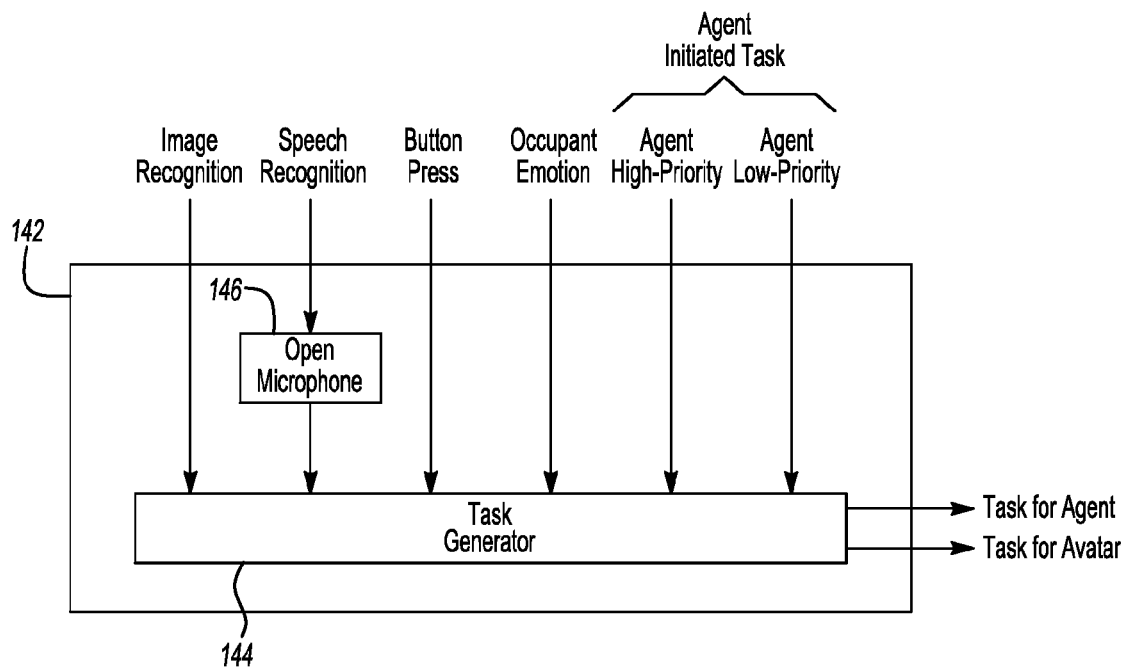
FIG. 11 is another block diagram of the spoken dialog manager of FIG. 10.

Referring now to FIG. 11, the algorithms/rules discussed above may be implemented in a task generator 144 as software or firmware. Other suitable alternatives, however, are also contemplated.

The task generator 144 of FIG. 11 serially queues the multiple inputs, e.g., speech recognition, occupant emotion, etc., and processes them to generate tasks. Any text to be spoken by the avatar is created within the task generator 144 of FIG. 11 by selecting text from a set of pre-programmed statements, an agent, or may be synthesized using optimality theory techniques. The text may also be produced in an abstract "meaning language" like First Order Predicate Calculus such that an emotional speech synthesizer, discussed below, may create the emotionally tagged text. Any actions that need to be performed are selected from a list of available actions. Actions may be made available by agents or modules, e.g., plug-n-play modules, discussed herein. A priority and any triggering event for the task is determined by rules, such as those described above. These components of the task are assembled into an EAS protocol message that is sent to a task manager, discussed in more detail below. Of course, any suitable protocol, such as XML, may be used.

As illustrated, the agent initiated tasks may be classified into high-priority and low-priority tasks. In some embodiments, this classification may be assigned by the agent generating the task using techniques similar to those described above with reference to the task generator 144. For example, algorithms associated with a safety agent that, inter alia, monitors the wheel slip and speed of the vehicle 14 may assign a high-priority to a task it generates indicative of a request to the driver to slow down because the road is slippery. In other embodiments, this classification may be assigned by the spoken dialog manager 142. For example, a task from a news agent that monitors various data sources accessible via the network 17 illustrated in FIG. 1 for news of interest to the occupant 12 also illustrated in FIG. 1 may be assigned a low-priority by the spoken dialog manager 142. Other configurations are also possible.

Agent tasks have a similar nature to button tasks and speech tasks in that they may alter the context of the dialog between the occupant and the EAS illustrated in FIG. 1.

As mentioned above, the EAS 10 illustrated in FIG. 1 includes open microphone functionality. An open microphone 146 facilitates the ability of the EAS 10 to receive instructions from the occupant 12 illustrated in FIG. 1 without the occupant 12 having to, for example, press a button. This open microphone system works in some embodiments because, as described above, the EAS 10 may be able to determine the number of occupants in the vehicle 14 illustrated in FIG. 1 and the location of these occupants using the OCS discussed above, to determine the location of the speaker using acoustics, to determine if the utterance it receives is in context, to determine if the occupant 12 is looking at the avatar using gaze detection, to remove the avatar's voice from the acoustic signal from the microphone using sound cancellation, etc. The open microphone may also be used with "barge-in" where the occupant can interrupt the avatar when necessary.

During an initial state entered, for example, upon vehicle start-up, algorithms implemented by the open microphone 146 listen for at least one of a limited number of words/statements, e.g., the name of the avatar, etc. Once detected, the open microphone 146 transitions into a conversational mode that allows it to accept a larger set of words/statements. As such, this transition is triggered, in this example, only by the voice of the occupant 12 illustrated in FIG. 1.

The larger set of words/statements that may be accepted in the conversational mode may be restricted by a context of the conversation. For example, statements made by the occupant 12 illustrated in FIG. 1 outside a current context may be ignored by the open microphone 146. In other embodiments, image recognition information, speech prosody, etc., may also be used to determine whether the speech is directed to the EAS 10 illustrated in FIG. 1. For example, if the occupant 12 is looking at another occupant (not shown) and speaking, the speech is likely not directed to the EAS 10. Likewise, if the speech of the occupant 12 is indicative of singing, such singing is likely not directed to the EAS 10. Therefore, the EAS 10 may be capable of determining whether it is a listener or an addressee of the occupant's speech.

Figure 12:
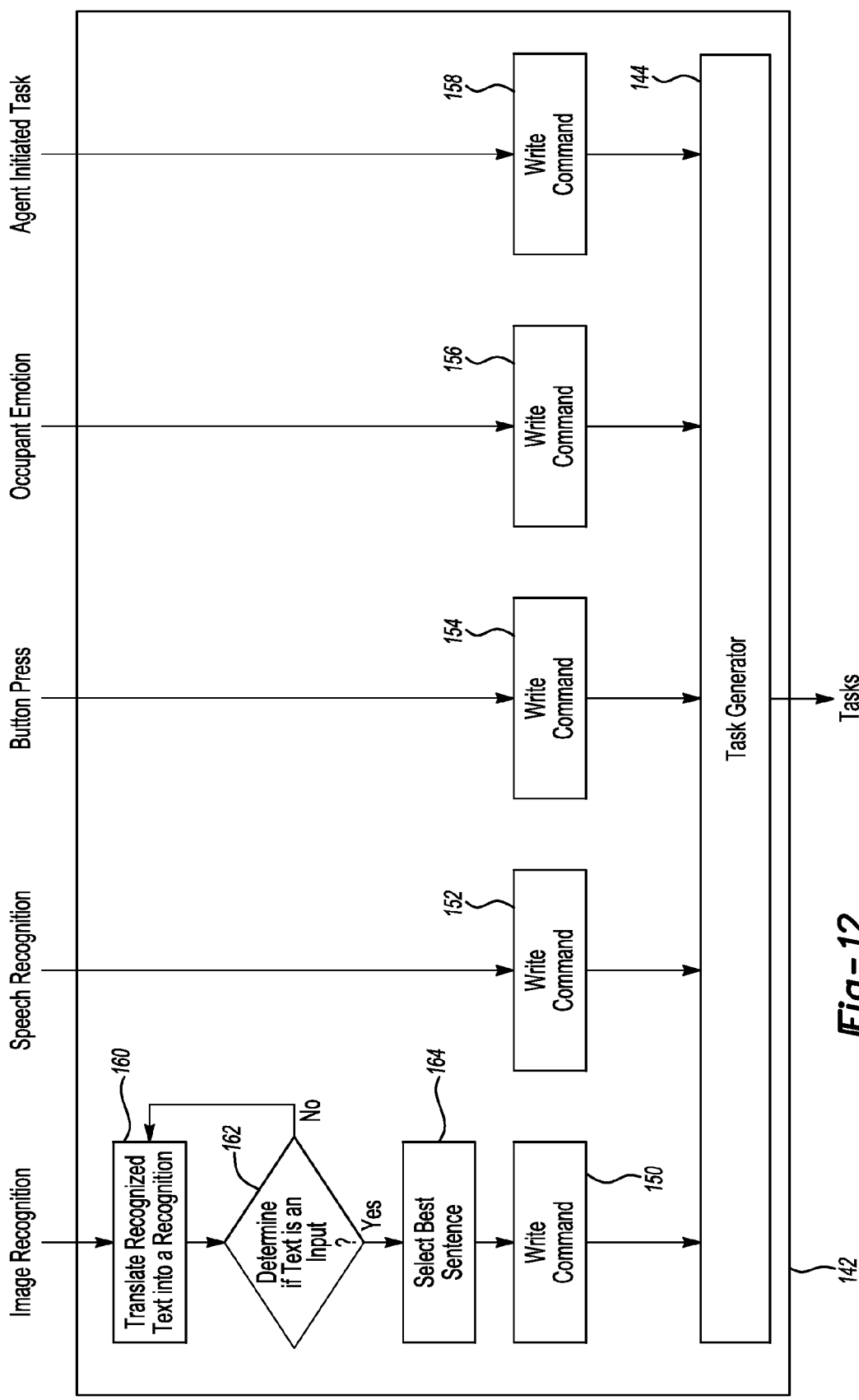
FIG. 12 is a flow chart depicting an algorithm employed by the spoken dialog manager of FIG. 10.

Referring now to FIG. 12, algorithms implemented by the task generator 144 evaluate inputs from each of the image recognition, speech recognition, button press, occupant emotion and agents in a serial fashion. That is, as the various types of inputs are received, they are blocked and evaluated sequentially, or in a "round robin" fashion, by the task generator 144. To enable this blocking function, the spoken dialog manager 142 includes respective write commands 150, 152, 154, 156, 158 for each of the types of input.

In other embodiments, algorithms implemented by the task generator 144 may evaluate inputs from each of the image recognition, speech recognition, button press, occupant emotion and agents, etc. based on time stamps associated with each input. These time stamps may be generated, for example, by any of the software modules 66 illustrated in FIG. 6 or elsewhere described herein. A time stamp may be determined by the state of the system clock (not shown) when the data is received. The task generator 144 sorts received inputs by their respective time stamps into a queue. Once queued, the task generator 144 may evaluate them as described above. Generally speaking, this an a application for a queuing algorithm such as Fair Queueing, Weighted Fair Queueing, Token Bucket, Round Robin, etc.

As apparent to those of ordinary skill, the speech recognition inputs of FIG. 12 require additional processing prior to being written to the task generator 144. As indicated at 160, the spoken dialog manager 142 translates any recognized speech in the form of text into a recognition, i.e., a set of hypotheses and an utterance recording associated with the recognized speech, using any suitable speech recognition engine, such as Nuance Recognizer, Nuance VoCon, SRI International DECIPHER, MIT Jupiter, etc. The spoken dialog manager 142 may then apply any one or more of a context, gaze direction, etc. to determine if the recognition is an input as indicated at 162.

In the embodiment of FIG. 12, the application of context via, for example, a finite state machine to the recognition may be performed to determine whether the occupant 12 illustrated in FIG. 1 is attempting to communicate with the EAS 10 or, for example, another occupant of the vehicle 14 illustrated in FIG. 1. If, for example, the recognition comprises "get me the news," the spoken dialog manager 142 may determine that the recognition is input, i.e., that the dialog is directed toward the EAS 10 illustrated in FIG. 1 and not, for example, another occupant in the vehicle 14. If, on the other hand, the recognition comprises "Hi, mom," the spoken dialog manager 142 may determine that such speech is not directed to it and return to 160.

As indicated at 164, the spoken dialog manager 142 then selects the best sentence from the recognition alternatives. For example, if a current conversation with the occupant 12 illustrated in FIG. 1 is regarding local restaurants, i.e., the spoken dialog manager 142 is in the restaurant context, it may select the "get me the reviews" phrase. It may be more probable that the occupant 12 would request reviews within the context of a conversation about restaurants as opposed to a request regarding the news.

As discussed above, the EAS 10 illustrated in FIG. 1 may convey a simulated emotional state. Algorithms/technologies/methods, etc. to facilitate such an emotional state are described with reference to FIGS. 13 through 15.

Figure 13:
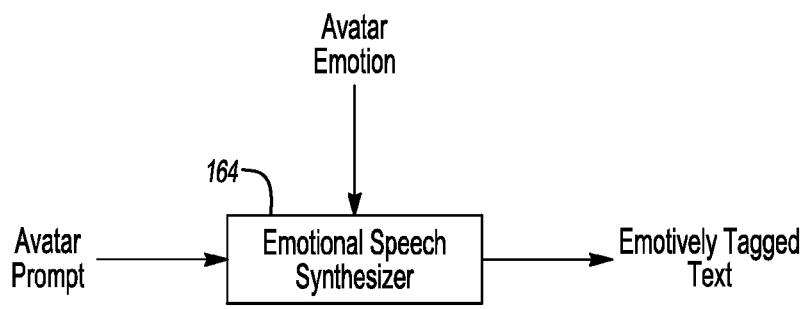
FIG. 13 is a block diagram of an emotional speech synthesizer for the emotive advisory system of FIG. 1.

Referring now to FIG. 13, an emotional speech synthesizer 164 combines the avatar emotion and avatar prompt, i.e., text for the avatar to speak, into emotively tagged text. As discussed above, in certain embodiments the avatar emotion has a vector representation. This vector representation is used by the emotional speech synthesizer 164 of FIG. 13 to mark-up portions of the text to be spoken by the avatar with indicators of emotion. These emotional markers are later interpreted by a text to speech engine, discussed below, in order to dynamically alter the prosody, tone, inflection, etc., with which the marked words are spoken. Such dynamic alteration of word pronunciation may convey emotional content in the speech.

If, for example, the avatar prompt includes the text "Have a nice day" and the avatar emotion is indicative of "calm," the emotional speech synthesizer 164 may output the emotively tagged text: "<speechstyle emotion="calm"> Have </speechstyle> a great day." Syntactically, the word "Have" is surrounded by the markers "<speechstyle emotion=calm>" and "</speechstyle.>" This designation signals the text to speech engine that the word "Have" has emotional content associated with it. (The phrase "a great day" does not have such content and will, as a result, be spoken in a neutral fashion.) Of course, other syntax schemes may be used. In this example, the word "Have" is marked to be spoken in a "calm" manner. As discussed below in detail, rules implemented in the text to speech engine may translate the emotive marker "calm" into a set of associated speed, pitch, pitch change, volume, high frequency content, etc., that will affect they way in which the word "Have" is spoken.

Other speech markers are defined in the Speech Synthesis Markup Language specification from the World Wide Web Consortium (W3C). Prosodic and emphasis elements that indicate avatar emotion are of the form "Have a <emphasis> nice </emphasis> day!" which would put the stress on the word nice. Other elements that may be implemented similarly are: the break element that may be used to simulate different articulation and pauses in the speech; and the prosody elements pitch, pitch contour, pitch range, speech rate, speech duration and speech volume (intensity). The ability to use these elements may be limited by the text to speech (TTS) technology used. The TTS may be a computer program and may typically use concatenative, articulation modeling, format synthesis or domain-specific synthesis, etc. It may also be a mechanical device that is acoustically similar to the human vocal tract.

The choice of speech synthesizer may have an impact on the naturalness of the voice which in turn impacts the actual words chosen for the speech. If the voice sounds mechanical like it comes from a computer, the use of words such as "I" and "me" should be limited. If the computer voice is very natural, as in the case of domain-specific synthesis, "I" and "me" may be used more readily.

The mechanical nature of the voice may be part of the persona of the EAS 10 illustrated in FIG. 1 which may also be linked to the appearance of the avatar. The emotional speech synthesizer 164 may have the ability to replace the phraseology of the text to reflect passive-active voice, introspection-extrospection, active emotional state-passive emotional state, positive or negative emotional valance, anger, rage, frustration, happiness, etc. Thus the emotional speech synthesizer 164 may be capable of replacing words and syntax, and inserting the correct prosody for a particular avatar emotion, weaving the explicit meaning of the text with the implicit emotion that should also be conveyed.

In certain embodiments, algorithms associated with the emotional speech synthesizer 164 are implemented in a finite state transducer that accepts the non-emotional speech as a lexical tape and the emotional state of the avatar as inputs. It first processes the input using semantic analysis, to create a meaning representation of the text. Meaning representations may take several forms, such as First Order Predicate Calculus, Semantic Networks, Conceptual Dependency Diagrams, frame-based representations, etc. This yields a representation of the literal meaning of the sentences. The emotional speech synthesizer 164 may include a catalog of emotional tagged sentences that the avatar can make and for which the literal meanings and the emotion have been computed. The emotional speech synthesizer 164 matches the literal meaning of the cataloged sentences and the current avatar emotion to select emotionally tagged sentences to be sent to the avatar. The emotional speech synthesizer 164 may also generate new sentences based on synonym substitution and using techniques such as those of optimality theory.

Algorithms implemented in the emotional speech synthesizer 164 may also modify the pronunciation of words (such as changing the pronunciation of the word "the" to either "thee" or "th[schwa]" and set accented syllable using allophonic transcription rules that incorporate the emotion of the avatar. The allophones created in this process may be represented by a allophonic alphabet such as the International Phonetic Alphabet (IPA), ARPAbet, etc. Dictionaries of pronunciation such as PRONLEX, CMUdict, CELEX, etc. are also widely available.

Algorithms implemented in the emotional speech synthesizer 164 may then take the sentences created by the above processes and choose among the sentences created by the above processes that best fit rules of syntax, language orthography, emotion, etc., in addition to maintaining historical information about which sentences have been used in the past to avoid repetition (which may become annoying over time). The selected sentence may then be output from the emotional speech synthesizer 164 for processing by the TTS.

Figure 14A:
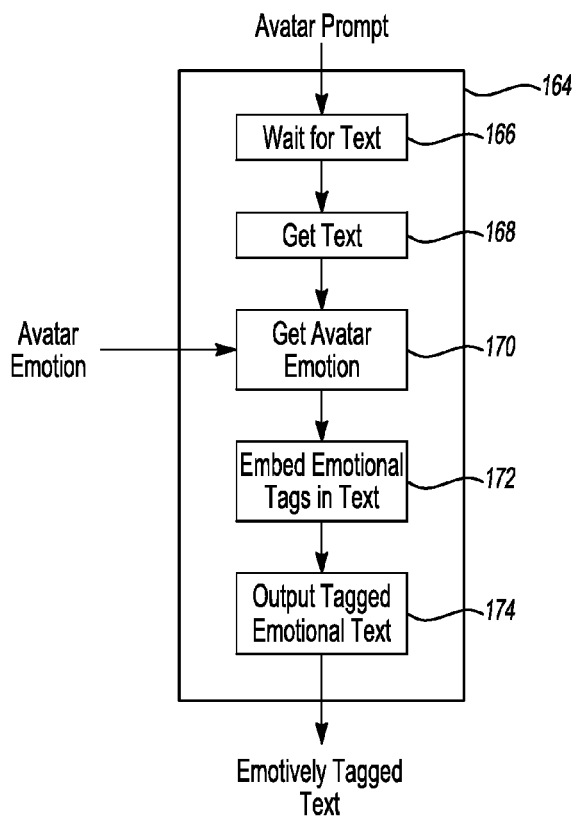
FIGS. 14A and 14B are flow charts depicting algorithms employed by the emotional speech synthesizer of FIG. 13.
Figure 14B:
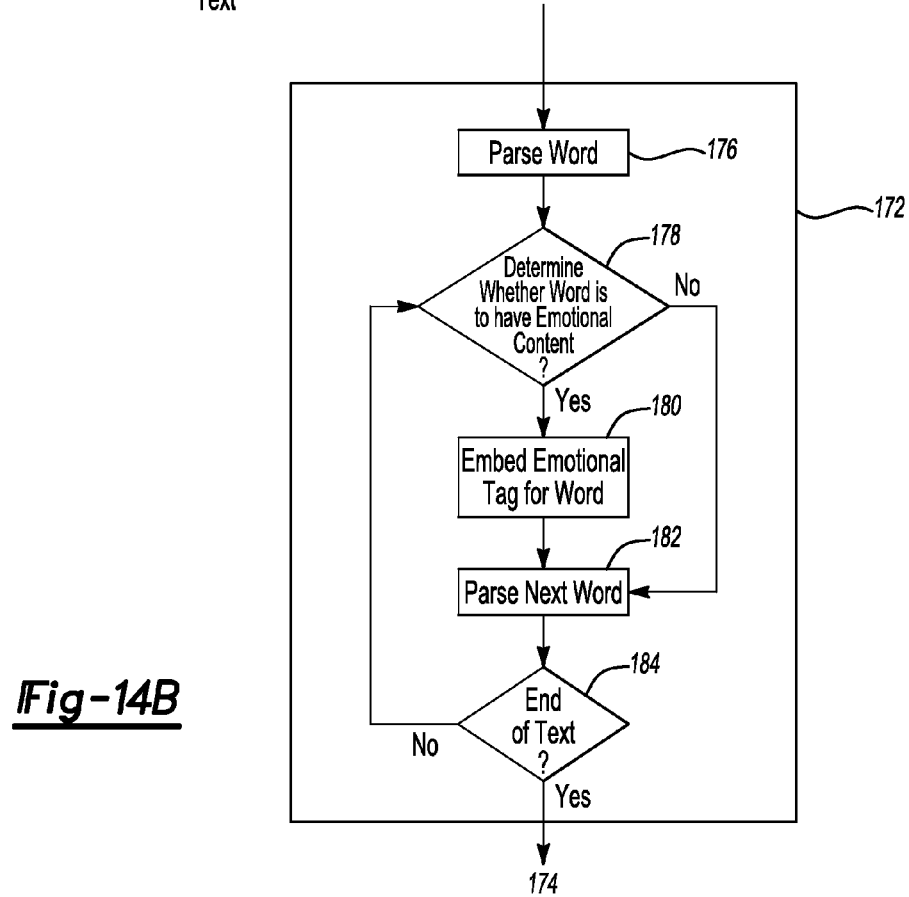

Referring now to the algorithms of FIGS. 14A and 14B, the emotional speech synthesizer 164 waits for text from the avatar prompt as indicated at 166. As indicated at 168, when text is detected, the emotional synthesizer 164 gets the text and then, as indicated at 170, gets the avatar emotion. As indicated at 172, the emotional speech synthesizer 164 embeds emotional tags in the text. As indicated at 174, the emotional speech synthesizer 164 outputs the emotively tagged text.

As indicated at 176, the first word of the text is parsed. A determination is made as to whether the parsed word is to have emotional content as indicated at 178. In the embodiment of FIG. 14B, this determination is based on the parsed word and the avatar emotion. For example, a database including key words mapped with emotions may be consulted to determine whether a particular word is to have emotional content. The database may include the word "have" associated with the emotions "calm" and "happy." Rules implemented by the emotional speech synthesizer 164 may indicate that if the parsed word is "have" and the avatar emotion is indicative of "calm" or "happy," then the word "have" will be marked with emotion indicated by the avatar emotion. If, however, the avatar emotion is indicative of emotions other than "calm" or "happy," then the word "have" will not be so marked. (Lexical emotional analysis techniques, for example, may be used to determine which words in the database are to have emotional content.)

In embodiments implementing the above described scheme, a particular word may or may not have emotional content depending upon the emotion associated with the avatar. In other embodiments, rules may be implemented that direct the emotional speech synthesizer 164 to mark the first parsed word of the text with the emotion of the avatar, or, to mark the first verb encountered in the text with the emotion. Other configurations and techniques are, of course, also possible.

If the parsed word is to be emotively tagged, the emotional speech synthesizer 164 embeds the emotional tag with the parsed word as indicated at 180. As indicated at 182, the next word of the text is parsed. A determination is then made as to whether the end of the text has been reached as indicated at 184. If yes, the process proceeds to 174. If no, the process returns to 178.

Returning to 178, if the parsed word is not to be emotively tagged, the process proceeds to 182.

Figure 15:
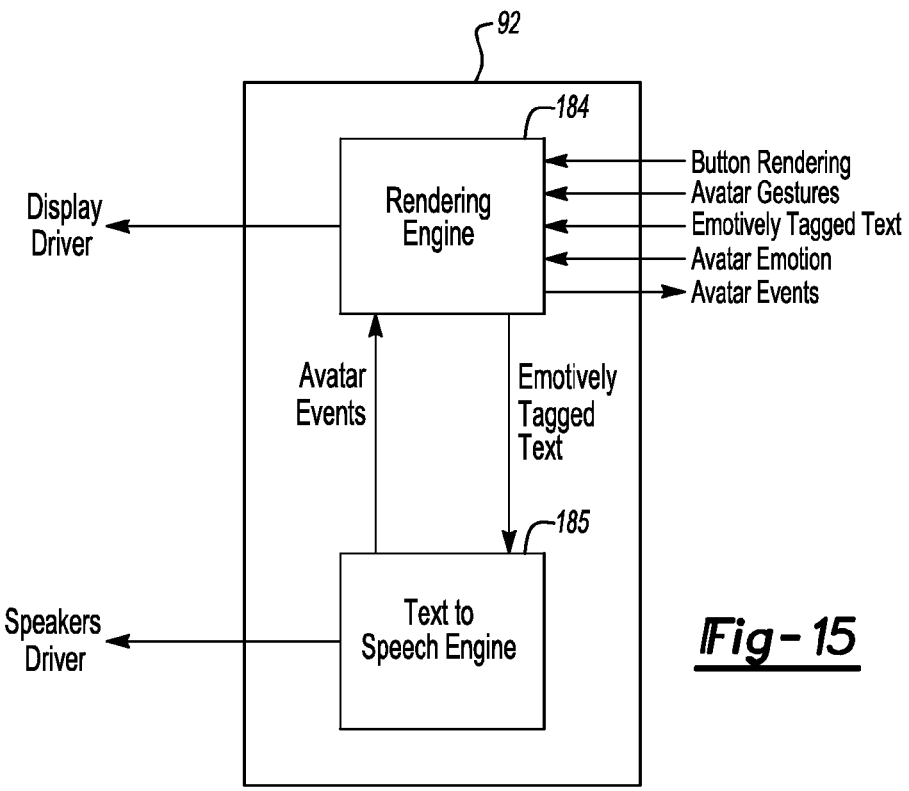
FIG. 15 is a block diagram of a display rendering engine and text-to-speech engine for the emotive advisory system of FIG. 1.

Referring now to FIG. 15, the avatar controller 92 may include a rendering engine 184, e.g., Renderware, Torque Game Engine, TV3D, 3D Game Studio, C4 Engine, DX Studio, Crystal Space, Game Blender, etc. (some of these use several graphics oriented APIs including Direct3D, OpenGL, DirectX, SDL, OpenAL, etc.), and a text to speech engine 185, e.g., Nuance Recognizer, Nuance VoCon, SRI International DECIPHER, MIT Jupiter, etc., implemented in software. Of course, the engines 184, 185 may be implemented in firmware, hardware, etc. as desired. As discussed above, the rendering engine 184 renders appropriate virtual buttons for the display 40 illustrated in FIG. 2 based on the button rendering input. Likewise, the rendering engine 184 renders appropriate avatar movements, e.g., hand movements, head movements, etc., for the display 40 based on the avatar gestures input.

In the embodiment of FIG. 15, the rendering engine 184 receives the emotively tagged text and provides it to the text to speech engine 185. The text to speech engine 185 may then perform concatenative synthesis of the avatar's voice with an emotional speech database and post processing for prosody.

The text to speech engine 185 may include a database (not shown) of allophones recorded with emotional voices, stored, for example, in Linear Predictive Coding (LPC) or cepstral form and indexed by the emotion as well as by the allophone itself. An entry in such a database for the emotion "calm" may dictate a set of prosody, tone, pitch, speed, etc. parameters that are applied to a word emotively tagged with the emotion "calm." Another entry in the database for the emotion "sad" may dictate another set of prosody, tone, pitch, speed, etc. parameters that are applied to a word emotively tagged with the emotion "sad."

Algorithms implemented in the text to speech engine 185 may select allophones from the database on the basis of the intended articulated sound and the required prosody, decode the allophones adjusting the duration, pitch, pitch profile, etc., then concatenate the allophones into speech followed by digital signal processing that smoothes the boundaries of the allophones and adds other emotional prosody effects like the rising pitch at the end of a sentence or an accent on a particular syllable.

Avatar events are generated by the text to speech engine 185 and provided to the rendering engine 184. In the embodiment of FIG. 15, the avatar events include visemes, syllables, words, sentences and paragraphs. Other and/or different avatar events may also be used. The text to speech engine 185 of FIG. 15 includes a mapping of phonemes with corresponding visemes. An avatar event indicative of a viseme is sent to the rendering engine 184 each time digital audio data indicative of a phoneme is output for the speakers driver 80 illustrated in FIG. 6. Likewise, an avatar event indicative of a word is sent to the rendering engine 184 each time digital audio data indicative of a word has been output for the speakers driver 80, etc. As an example, digital audio data indicative of the sentence "How are you?" would result in the following stream of avatar events (assuming there are two visemes associated with the word "How," one viseme associated with the word "are" and two visemes associated with the word "you"): viseme, viseme, syllable, word, viseme, syllable, word, viseme, viseme, syllable, word, sentence.

The rendering engine 184 of FIG. 15 includes a mapping of visemes, etc. with corresponding lip positions. As apparent to those of ordinary skill, a stream of avatar events may inform the rendering engine 184 as to the lip positions that correspond to the digital audio data output for the speakers driver 80 illustrated in FIG. 6.

As discussed in more detail below, the avatar events may be used as a timing basis to determine if/when to interrupt current speech of the avatar with speech of a more urgent nature. For example, avatar speech may be interrupted on the next viseme, syllable, word, sentence, paragraph, etc. As such, the rendering engine 184 outputs avatar events received from the text to speech engine 185 to, inter alia, inform other modules discussed herein as to the state of the speech associated with the avatar.

As discussed above, the rendering engine 184 may translate the avatar emotion into a set of facial expressions/colors/etc. corresponding to the avatar emotion. The rendering engine 184 of FIG. 15 includes a database that maps emotions with facial positions. For example, the database may include an entry that maps the emotion "angry" with the color red such that the avatar turns red when it is angry. The database may also include an entry the maps the emotion "envy" with the color green such that the avatar turns green when it is envious. Similarly, positions of various features or the features themselves may be altered with emotion. Other configurations are also possible.

In other embodiments, the rendering engine 184 may interpret the emotively tagged text before providing it to the text to speech engine 185 in order to determine how to alter the appearance of the avatar. Using a previous example, algorithms implemented in the rendering engine 184 may interpret the emotively tagged text "<speechstyle emotion="calm"> Have </speechstyle> a great day." in order to determine that the avatar is to convey the emotion "calm." Of course, other and/or different syntaxes for the emotively tagged text may be used to facilitate interpretation by the rendering engine 184. For example, the avatar emotion may be appended onto the end of emotively tagged text. The rendering engine 184 may parse the text, remove the avatar emotion and provide the resulting tagged text to the text to speech engine 185.

As discussed above, the EAS 10 illustrated in FIG. 1 may learn to anticipate requests, commands and/or preferences of the occupant 12 also illustrated in FIG. 1 based on a history of interaction between the occupant 12 and the EAS 10. Techniques/algorithms/methods, etc. to enable such learning are discussed with reference to FIGS. 16 through 17C.

Figure 16:
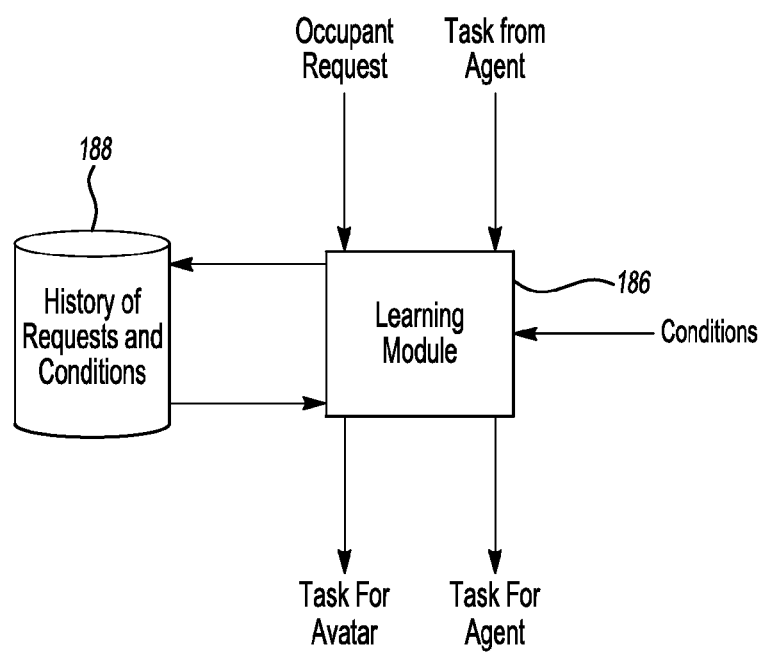
FIG. 16 is a block diagram of a learning module for the emotive advisory system of FIG. 1.

Referring now to FIG. 16, an EAS learning module 186, implemented in software, firmware, etc. receives occupant requests directed to the EAS 10 illustrated in FIG. 1. The requests and associated conditions (some of which are illustrated in FIG. 6) under which the requests were made are recorded in a database 188. For example, the learning module 186 may record that, on four separate occasions, a driver set the cruise control of the vehicle 14 illustrated in FIG. 1 after having traveled for at least 1 minute at 60 miles an hour.

In some embodiments, the learning module 186 is an intelligent system that implements algorithms that first uses approximate reasoning to determine what action is needed and then learns by: observing when the occupant 12 illustrated in FIG. 1 selects a particular action; suggesting the occupant 12 take an action and learning from the occupant's response; observing when the occupant 12 cancels an action the EAS 10 illustrated in FIG. 1 initiated automatically, etc.

As discussed above, the conditions recorded may be any of the speech recognition outputs, image recognition outputs, button press, vehicle system outputs, etc. illustrated in FIG. 6. Other conditions, such as geographic location, weather information, occupant emotion, avatar emotion, etc., may also be recorded as desired.

As explained below, the learning module 186 compiles this request and condition information to anticipate future requests and/or to filter agent generated tasks. Once compiled, the learning module 186 may create at least one task for the avatar and/or an agent based on a set of recognized conditions.

Continuing with the above example, the learning module 186 may provide a rule that specifies that if the cruise control is set at least four times while continuously holding a fixed speed on the highway (requiring information from the navigation system and wheel speed data processed using statistical process control), an avatar task will be generated to ask the driver if they would like the cruise control set once the speed of the vehicle 14 illustrated in FIG. 1 reaches 60 miles an hour. In this example, the learning module 186 now has a record of such conditions and the record satisfies the rule. As a result, the learning module 186 may generate the task described using techniques described herein. The spoken dialog manager 142 illustrated in FIG. 10 may interpret an affirmative response to such a query and, as a result, generate a task for a powertrain agent to implement cruise control.

The learning module 186 may record responses to requests similar to those described in the above example to further learn from the occupant 12 illustrated in FIG. 1. Still continuing with the above example, the learning module 186 may further provide a rule that specifies that if the driver affirmatively responds to such queries three times, the cruise control should automatically be set and the driver informed such is being done. Likewise, the learning module 186 may also provide a rule that specifies that if the driver negatively responds to such requests two times, the driver should no longer be queried regarding the cruise control for a period of 2 weeks. Other and/or different rules may, of course, be implemented within the learning module 186.

In other embodiments, the database 188 may include a set of pre-specified conditions and associated tasks. Each time a task is implemented, the pre-specified conditions are checked. If the pre-specified conditions are met, a counter is incremented. Once the counter achieves a threshold value, a rule, for example, may specify that the next time the conditions occur, the learning module 186 is to generate a task to query the occupant 12 illustrated in FIG. 1 as to whether they wish the task to be completed or to complete the task and inform the occupant 12 that the task was completed, etc. As an example, the database 188 may include a first task entry of "set cruise control" and an associated condition of "speed greater than 60 miles per hour." The database 188 may also include a second task entry of "set cruise control" and an associated condition of "speed greater than 10 miles per hour and less than 20 miles per hour." A counter is also provided with each of these entries. If the cruise control is set on three separate occasions at speeds respectively of 65 miles per hour, 68 miles per hour and 60 miles per hour, the counter associated with the first task entry will have been incremented three times while the counter associated with the second task entry will not have been incremented. Assuming a threshold value of three, the next time the speed of the vehicle 14 illustrated in FIG. 1 exceeds 60 miles per hour, a rule implemented in the learning module 186 may trigger the generation of a task, using the techniques described herein, that will prompt the EAS 10 illustrated in FIG. 1 to query the occupant 12 as to whether they wish the cruise control to be set. As another example, the database 188 may include a task entry of "turn on classical music" and an associated condition of "occupant emotion=angry." If the occupant 12 plays classical music, for example, on four separate occasions when the occupant emotion is "angry," the next time the occupant emotion is "angry," the EAS 10 may play classical music (or ask the occupant 12 if they would like to hear classical music if the rule permits.) Of course, other EAS behaviors, vehicle operating parameters, etc. may also be altered in a manner similar to that described above.

In still other embodiments, analytical techniques may be used to generate rules that permit the learning module 186 to learn from the occupant 12 illustrated in FIG. 1. For example, the learning module 186 may implement a neural network that monitors the condition inputs and attempts to match patterns of conditions with occupant requests. Such a neural network may recognize, for example, that at a particular time of day, a certain driver asks for news about financial markets. As a result, the learning module 186 may generate a task for an agent to gather such news about financial markets in advance of the particular time of day and generate a task to ask the driver just before that particular time of day if they would like the news about financial markets. In this example, the neural network may further recognize that after several negative responses to such learning module 186 initiated requests, the neural network may no longer gather such news or prompt the driver regarding such news in advance of the particular time of day. Likewise, several affirmative responses to such requests may reinforce this behavior governed by the neural network. Other suitable techniques, however, may also be used.

As mentioned above, the learning module 186 may filter agent generated tasks consistent with the compiled information from the database 188. For example, a fuel economy agent may be configured to prompt the avatar to ask, as a default, that the vehicle be put in fuel economy mode at engine start-up. Compiled information from the database 188 may reveal a record of affirmative or negative responses to such requests. If, for example, the learning module 186 compiles a set of mostly negative responses, the learning module 186 may terminate the fuel economy agent initiated task. If, for example, the learning module 186 compiles a set of mostly affirmative responses, the learning module 186 may generate a task that automatically puts the vehicle 14 into fuel economy mode and merely informs the driver that it is doing so.

The EAS 10 illustrated in FIG. 1 may also download its learned preferences from the learning module 186 to one or more of the servers 16*n* illustrated in FIG. 1. The one or more servers 16*n* may aggregate this information with other such information from other EAS. The EAS 10 may then request this aggregated preference information to pre-load/update the learning module 186 with the collective experience of numerous EAS.

Figure 17A:
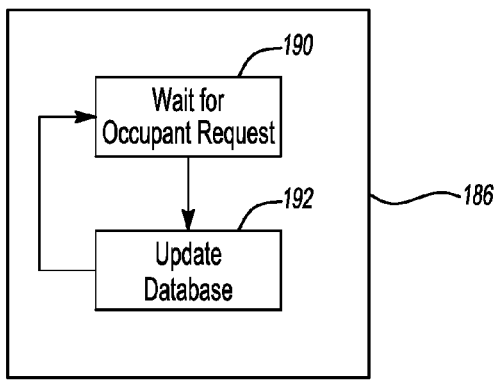
FIGS. 17A through 17C are flow charts depicting algorithms employed by the learning module of FIG. 16.

Referring now to the algorithm of FIG. 17A, a thread of the learning module 186 waits for an occupant request as indicated at 190. As indicated at 192, the thread updates the database 188 with the instant conditions when an occupant request is received.

Figure 17B:
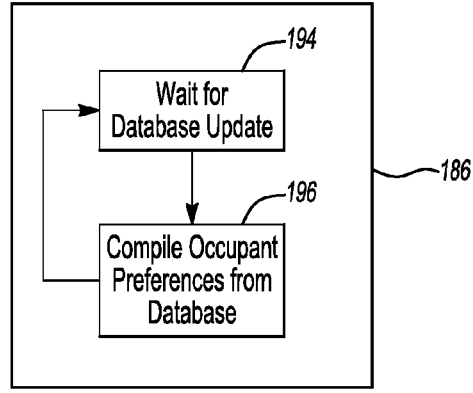

Referring now to the algorithm of FIG. 17B, another thread of the learning module 186 waits for an update to the database 188 as indicated at 194. As indicated a 196, the thread compiles occupant preferences from the database 188 when then database 188 is updated.

Figure 17C:
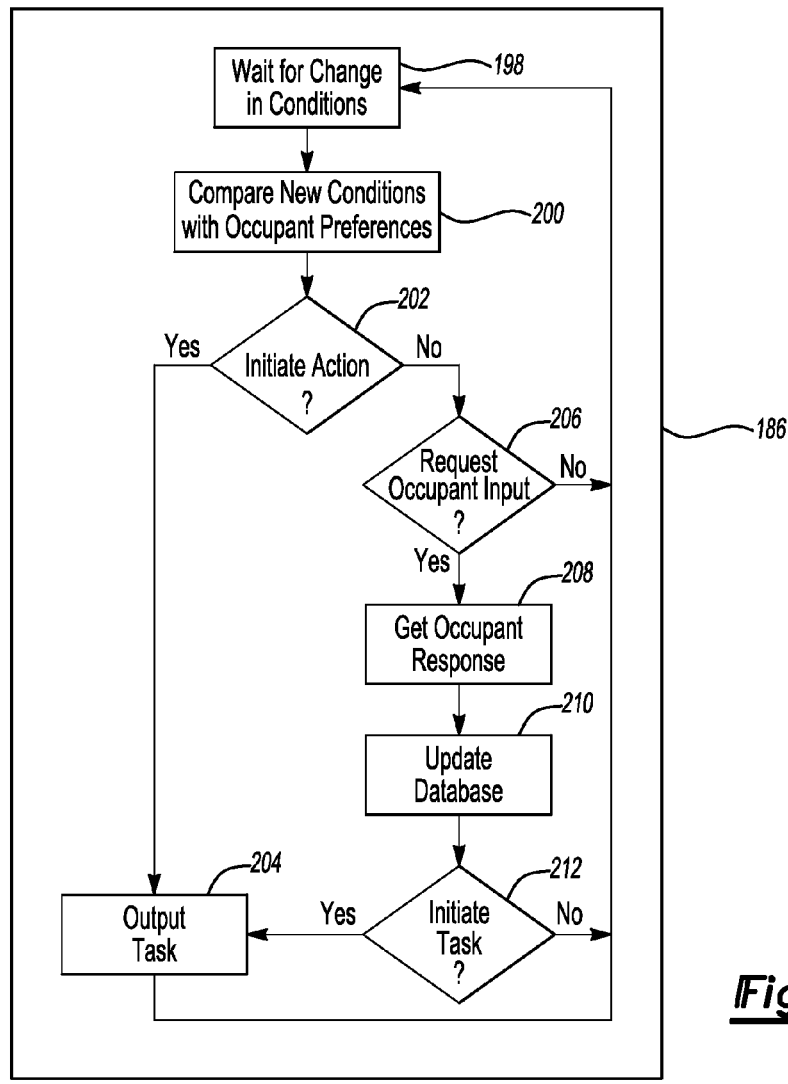

Referring now to the algorithm of FIG. 17C, yet another thread of the learning module 186 waits for a change in input conditions as indicated at 198. As indicated at 200, when a change occurs, the thread compares the new conditions with any occupant preferences compiled previously at 196. The thread then determines whether to initiate an action as indicated at 202. For example, the thread may determine that a current set of conditions fulfill a particular rule similar to the rules discussed above. If yes, the thread outputs a task as indicated at 204. The thread then returns to 198. If no, the thread then determines whether to request occupant input as indicated at 206. For example, the thread may request such input if a rule specifies that a task for an action may be initiated if the occupant provides an affirmative response to an inquiry. If no, the thread returns to 198. If yes, the thread gets the occupant response as indicated at 208. As indicated at 210, the thread updates the history database 188. The thread then determines whether to initiate the task as indicated at 212. This determination may depend upon, for example, whether the occupant 12 illustrated in FIG. 1 provided an affirmative response. If yes, the thread proceeds to 204. If no, the thread returns to 198.

Various tasks generated by differing modules have been discussed above. Techniques/methods/algorithms, etc. that may be used to prioritize and execute such tasks are discussed with reference to FIGS. 18 through 20.

Figure 18:
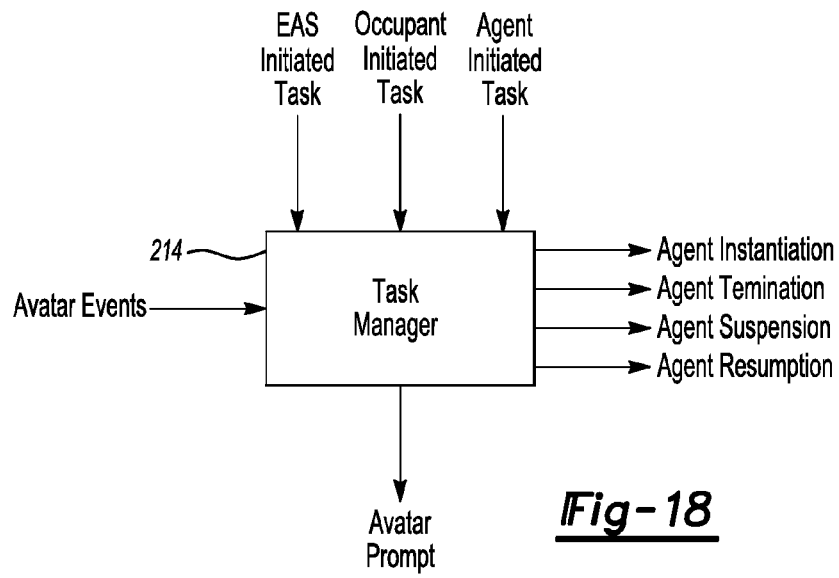
FIG. 18 is a block diagram of a task manager for the emotive advisory system of FIG. 1.

Referring now to FIG. 18, a task manager 214 manages the resources associated with the EAS 10 and vehicle 14 both illustrated in FIG. 1 and demanded by the various tasks described above. In certain embodiments, the avatar may only engage in one task at a time. As such, algorithms implemented by the task manager 214 schedule and execute the tasks related to the use of the avatar based on a priority scheme. This priority scheme, inter alia, dictates whether a certain task may be performed immediately, thus interrupting any current task, or may be performed at some later time. As discussed below, the avatar may be interrupted to perform a task or may begin a new task once a current task is complete. The task manager 214 thus balances the use of the avatar with the load placed upon it by the various actors within the system described herein.

The task manager 214 may receive EAS initiated tasks, occupant initiated tasks and/or agent initiated tasks, etc. The task manager 214 then queues and executes them accordingly. In some embodiments, the task manager 214 queues each of the tasks based on its priority and executes each of the tasks based on this priority. Because the task manager 214 may interrupt a current task to execute a higher priority task, it may terminate, suspend and/or resume the current task.

As discussed above, avatar events, e.g., visemes, syllables, words, etc. are received and used by the task manager 214 of FIG. 18 as a basis to determine when to execute the queued tasks (provided that any triggering event(s), discussed below, have been met). For example, a high priority task may interrupt a current task upon a next syllable of the avatar. A medium priority task may be performed at the end of a sentence of the avatar. A low priority task may be performed when there are no other higher priority tasks to be performed.

The execution of a task may involve one or more agents. For example, a task may involve a news agent that collects news from information sources available via the web. Such agents may need to be interrupted if, for example, they require avatar resources. As a result, the task manager 214 of FIG. 18 may output agent instantiation, termination, suspension, resumption, etc. commands. The execution of a task may further involve text for the avatar to speak. The task manager 214 outputs such text via the avatar prompt.

Figure 19:
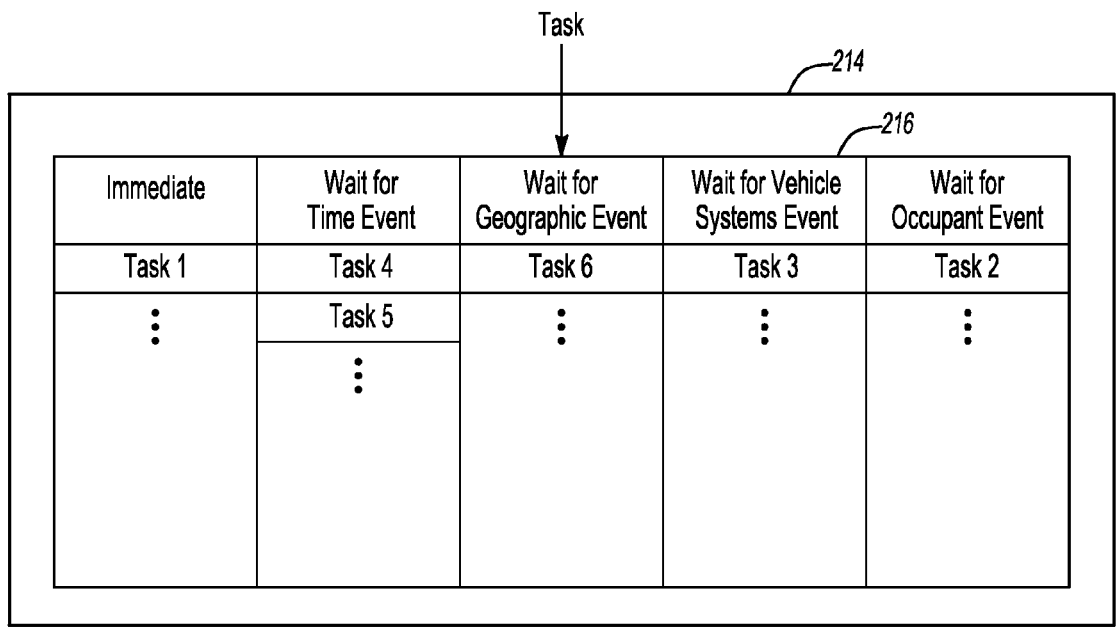
FIG. 19 is another block diagram of the task manager of FIG. 18.

Referring now to FIG. 19, a task queue 216 may be used to queue the tasks managed by the task manager 214 based on, for example, the priority and any triggering events associated with the tasks. In the embodiment of FIG. 19, the triggering events are represented as various bins within the task queue 216. For example, a task that lacks a triggering event may be binned as an "Immediate" task, e.g., "Task 1." A task that should be performed in the vicinity of a gas station may be binned as a "Wait For Geographic Event," e.g., "Task 2." A task that should be performed when tire pressure is less than a certain value may be binned as a "Wait For Vehicle Systems Event," e.g., "Task 3." Other and/or different binning techniques may, of course, be used.

Within a particular bin, each task is ordered based upon a specified avatar event embedded with the task. As discussed above, avatar events may include visemes, syllables, words, sentences, paragraphs, etc. Those tasks that are to be performed upon the next viseme, e.g., "Task 4" will be executed before tasks that are to be performed upon the next paragraph, e.g., "Task 5." Thus when generated, each task may include information indicative of the avatar event that will trigger its execution.

As new tasks are received by the task manager 214, they are binned within the task queue 216. Within each bin, the tasks are then re-ordered, as necessary, depending upon the avatar event associated with each task.

Returning again to FIG. 18, tasks that are interrupted may be aborted, suspended or re-queued. A suspended task will continue from the point it was interrupted after completion of higher priority tasks. For example, if a news reading task is suspended, it will begin reading the news from where it left off when it was interrupted. A re-queued task will restart after completion of higher priority tasks. For example, if the news reading task is re-queued, it will start, when executed, from the beginning of its news cast.

Aborting, suspending and re-queuing tasks may require the task manager 214 to instantiate, terminate, suspend or resume one or more agents. As discussed below, if a task requires an agent that is not instantiated, the task manager 214 may issue a command to instantiate an agent when, for example, a triggering event for the task occurs. Any current agents consuming avatar resources may need to be terminated or suspended if a higher priority task is to be executed. The termination and suspension commands discussed above are issued by the task manager 214 under such circumstances. If an agent is suspended, it may later be resumed via a resumption command as discussed above.

Multiple tasks may be suspended under circumstances where multiple agents have yet to complete their tasks and also require avatar resources. In some embodiments, the task manager 214 may sequentially issue resumption commands to resume agents in order of their priority. Other schemes, however, may also be used.

Figure 20A:
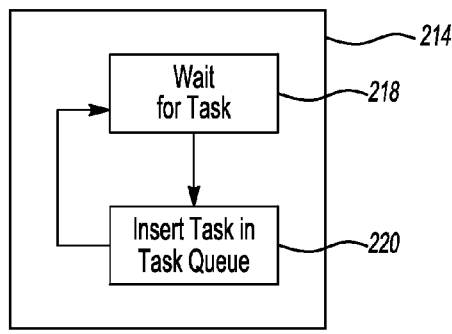
FIGS. 20A and 20B are flow charts depicting algorithms employed by the task manager of FIG. 18.

Referring now to the algorithm of FIG. 20A, a thread of the task manager 214 waits for a task as indicated at 218. As indicated at 220, the thread inserts the task in the task queue 216 when received. The thread then returns to 218.

Figure 20B:
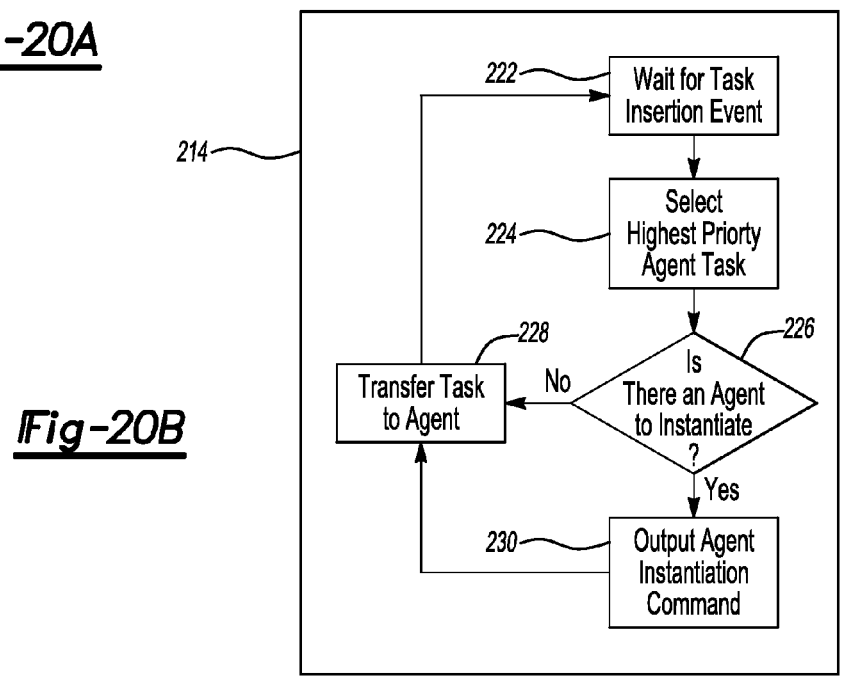

Referring now to the algorithm of FIG. 20B, another thread of the task manager 214 waits for a task to be inserted into the task queue 216 as indicated at 222. As indicated at 224, the thread selects the highest priority agent task (based on triggering events as well as priority). As indicated at 226, the thread determines whether there is an agent to instantiate. If no, the thread transfers the task to the appropriate agent as indicated at 228. The thread then returns to 222. If yes, the thread outputs an agent instantiation command as indicated at 230. The thread then proceeds to 228. Similar threads may be configured to select and execute avatar tasks.

Various agents have been discussed herein. In certain embodiments, agents are programs that may interface with the EAS 10 illustrated in FIG. 1. These programs, as described above, may perform certain, and is some cases specialized, functions, algorithms, etc.

Figure 21:
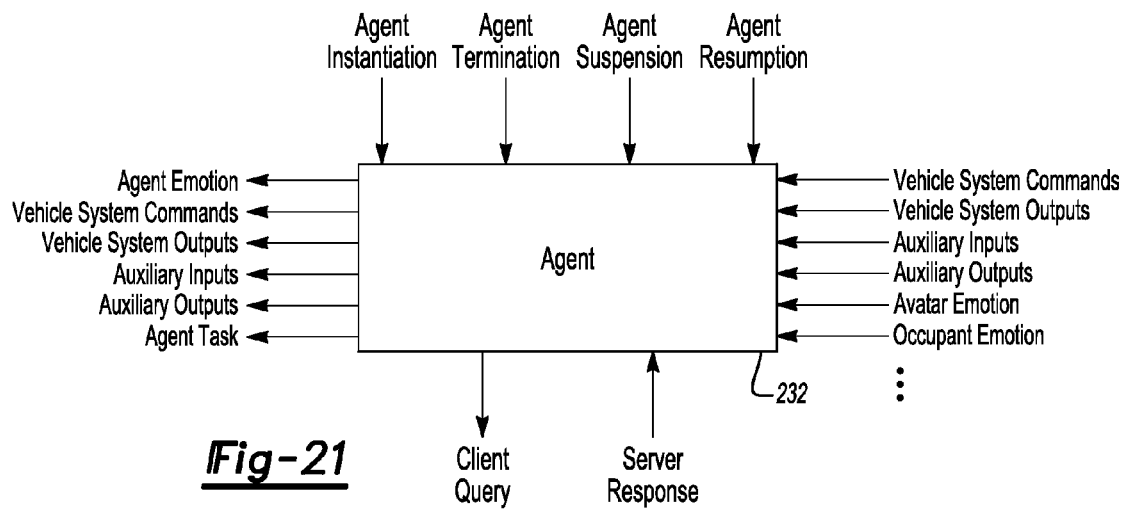
FIG. 21 is a block diagram of an agent configured to interact with the emotive advisory system of FIG. 1.

Referring now to FIG. 21, an agent 232 may be configured to receive a variety of inputs. The agent 232 may process these inputs, provide a variety of outputs and perform its designated task(s) in accordance with the inputs. For example, a driver's training agent may train the occupant 12 of the vehicle 14 both illustrated in FIG. 1, via audio and visual feedback, to drive the vehicle 14 so as to maximize its usable lifetime. The agent 232 may process vehicle system outputs to determine, for example, if the occupant 12 frequently aggressively brakes and warn the driver that such behavior may adversely affect any braking system associated with the vehicle 14. To facilitate such feedback, the agent 232 may include a task generator (not shown) similar to those described herein to generate the necessary tasks for the avatar to convey the feedback.

As discussed above, the agent 232 may also output an emotional output, e.g., agent emotion, that, in certain embodiments, is an indicator of how well the agent 232 is performing its intended function.

Some agents run as independent programs that use the middleware message passing system discussed herein to interact with the EAS 10 illustrated in FIG. 1. They generally have intelligence and have the same status in the EAS 10 as the occupant 12 illustrated in FIG. 1 or the learning module 186 illustrated in FIG. 16.

While embodiments of the invention have been illustrated and described, it is not intended that these embodiments illustrate and describe all possible forms of the invention. The words used in the specification are words of description rather than limitation, and it is understood that various changes may be made without departing from the spirit and scope of the invention.

What is claimed:

1. An emotive advisory system for use by an occupant of an automotive vehicle, the system comprising:
   a computer configured to
   receive input indicative of an operating state of the vehicle and input indicative of an emotional state of the occupant,
   generate data representing an avatar having an appearance and data representing a spoken statement for the avatar having at least one speech characteristic, the appearance and the at least one speech characteristic (i) depending on at least one of the operating state of the vehicle and the emotional state of the occupant and (ii) conveying a simulated emotional state of the avatar to the occupant to prompt the occupant to pose a query regarding a cause of the avatar's simulated emotional state,
   receive input indicative of a query from the occupant regarding the avatar's simulated emotional state,
   in response to the query, generate data representing another spoken statement for the avatar and including information about the cause of the avatar's simulated emotional state, and
   output the data representing the avatar for visual display and the data representing the statements for the avatar for audio play.

2. The system of claim 1 wherein the computer is further configured to determine whether a predetermined event has occurred and to query the occupant via spoken dialog if the predetermined event has occurred.

3. The system of claim 2 wherein the computer is further configured to receive a spoken response from the occupant to the computer's query.

4. The system of claim 3 wherein the computer is further configured to alter an operating parameter of the vehicle based on the spoken response to the computer's query.

5. The system of claim 1 wherein the input indicative of an emotional state of the occupant is based on at least one of audio and visual characteristics of the occupant.

6. The system of claim 1 wherein the computer is further configured to determine whether a predetermined event has occurred, to access information from sources remote from the vehicle if the predetermined event has occurred and to provide at least a portion of the accessed information to the occupant visually or audibly.

7. An emotive information system for a user of an automotive vehicle, the system comprising:
   at least one sensor configured to detect at least one of audio and visual characteristics of the user;
   a computer configured to
      receive the detected information,
      receive information about an operating state of the vehicle, and
      generate data representing a simulated emotional state based on at least a portion of the received information; and
   an interface configured to convey the simulated emotional state to the user to prompt the user to pose a query regarding a cause of the simulated emotional state, wherein the computer is further configured to receive a query from the user regarding the simulated emotional state and generate data representing a response to the query including information about the cause of the simulated emotional state.

8. The system of claim 7 wherein the simulated emotional state is conveyed to the user via an avatar.

9. The system of claim 8 wherein the computer is further configured to selectively display the avatar based on an operating state of the vehicle.

10. The system of claim 7 wherein the computer is further configured to determine whether a predetermined event has occurred and to initiate a spoken dialog with the user if the predetermined event has occurred.

11. The system of claim 7 wherein the at least one sensor includes an open microphone.

12. The system of claim 7 wherein the at least one sensor is further configured to detect a button press from the user.

* * * * *